(12) United States Patent
Wang et al.

(10) Patent No.: US 9,084,693 B2
(45) Date of Patent: Jul. 21, 2015

(54) REDUCING CRIMPING DAMAGE TO A POLYMER SCAFFOLD

(71) Applicant: Abbott Cardiovascular Systems Inc., Santa Clara, CA (US)

(72) Inventors: Yunbing Wang, Sunnyvale, CA (US); Luis Vazquez, Lathrop, CA (US); Hung T. Nguyen, San Diego, CA (US); Scott H. Mueller, Escondido, CA (US); Kathleen Yan, Cupertino, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 14/024,572

(22) Filed: Sep. 11, 2013

(65) Prior Publication Data
US 2014/0008007 A1    Jan. 9, 2014

Related U.S. Application Data

(62) Division of application No. 12/861,719, filed on Aug. 23, 2010, now Pat. No. 8,539,663.

(51) Int. Cl.
*B29D 23/00* (2006.01)
*A61F 2/958* (2013.01)
*A61F 2/95* (2013.01)

(52) U.S. Cl.
CPC . *A61F 2/958* (2013.01); *A61F 2/95* (2013.01); *B29D 23/00* (2013.01); *A61F 2002/9522* (2013.01); *A61F 2250/0067* (2013.01); *Y10T 29/4994* (2015.01); *Y10T 29/49908* (2015.01); *Y10T 29/49925* (2015.01); *Y10T 29/49927* (2015.01); *Y10T 29/49945* (2015.01); *Y10T 29/53996* (2015.01)

(58) Field of Classification Search
CPC ... A61F 9/958; A61F 2/95; A61F 2002/9522; A61F 2250/0067; B29D 23/00; Y10T 29/4994; Y10T 29/49927; Y10T 29/49945; Y10T 29/49925; Y10T 29/53996; Y10T 29/49908
USPC ......... 29/525, 283.5, 515, 516, 523; 156/156; 623/1.15, 1.16
See application file for complete search history.

(56) References Cited

U.S. PATENT DOCUMENTS

| | | | |
|---|---|---|---|
| 5,261,263 | A  | 11/1993 | Whitesell |
| 6,360,577 | B2 | 3/2002  | Austin |
| 6,629,350 | B2 | 10/2003 | Motsenbocker |
| 6,783,542 | B2 | 8/2004  | Eidenschink |
| 6,805,703 | B2 | 10/2004 | McMorrow |
| 7,010,850 | B2 | 3/2006  | Hijlkema et al. |
| 7,316,148 | B2 | 1/2008  | Asmus et al. |

(Continued)

OTHER PUBLICATIONS

U.S. Appl. No. 12/561,971, filed Sep. 17, 2009, Trollsas et al.

(Continued)

*Primary Examiner* — John C Hong
(74) *Attorney, Agent, or Firm* — Squire Patton Boggs (US) LLP

(57) ABSTRACT

A medical device includes a polymer scaffold crimped to a catheter having an expansion balloon. The scaffold is crimped to the catheter by a multi-step process for increasing scaffold-catheter yield following a crimping sequence. Damage reduction during a crimping sequence includes modifying blades of a crimper, adopting a multi-step crimping sequence, and inflating a supporting balloon to support the scaffold during crimping.

20 Claims, 13 Drawing Sheets

(56) References Cited

U.S. PATENT DOCUMENTS

| | | | |
|---|---|---|---|
| 7,389,670 B1 | 6/2008 | Kokish et al. | |
| 7,530,253 B2 * | 5/2009 | Spenser et al. | 72/402 |
| 8,123,793 B2 | 2/2012 | Roach et al. | |
| 8,245,559 B1 * | 8/2012 | Warriner et al. | 72/402 |
| 8,323,760 B2 | 12/2012 | Zheng et al. | |
| 2004/0093720 A1 * | 5/2004 | Motsenbocker | 29/700 |
| 2005/0143752 A1 | 6/2005 | Schwager et al. | |
| 2005/0188525 A1 | 9/2005 | Weber et al. | |
| 2005/0229670 A1 | 10/2005 | Perreault | |
| 2007/0289117 A1 | 12/2007 | Huang et al. | |
| 2008/0127707 A1 | 6/2008 | Kokish et al. | |
| 2008/0275537 A1 | 11/2008 | Limon | |
| 2010/0004735 A1 | 1/2010 | Yang et al. | |

OTHER PUBLICATIONS

U.S. Appl. No. 12/772,116, filed Apr. 30, 2010, Jow et al.
U.S. Appl. No. 12/776,317, filed May 7, 2010, Wang.
U.S. Appl. No. 12/831,878, filed Jul. 7, 2010, Van Sciver.
International Search Report for PCT/US2011/048117, mailed Feb. 17, 2012, 19 pgs.
Angioplasty Summit Abstracts/Oral, The Am. J. of Cardiology, Apr. 23-26, 2013, p. 23B.
Bosiers et al., "Coronary and endovascular applications of the Absorb™ bioresorbable vascular scaffold", Interv. Cardiol. 4(6), pp. 621-631 (2012).
Miller "Abbott's Bioresorbable Stent Shows Durable Results in ABSORB Trial", The Gray Sheet, pp. 17-18, Mar. 2003.

* cited by examiner

9,084,693 B2

REDUCING CRIMPING DAMAGE TO A POLYMER SCAFFOLD

This is a divisional of U.S. application Ser. No. 12/861,719 filed Aug. 23, 2010, the contents of which are hereby incorporated by reference in its entirety for all purposes.

BACKGROUND OF THE INVENTION

1. Field of the Invention

The present invention relates to drug-eluting medical devices; more particularly, this invention relates to processes for crimping a polymeric scaffold to a delivery balloon.

2. Background of the Invention

Referring to FIG. 1A, there is shown a perspective view of a crimping assembly 20 that includes three rolls 123, 124, 125 used to position a clean sheet of non-stick material between the crimping blades and a metal stent prior to crimping. For example, upper roll 125 holds the sheet secured to a backing sheet. The sheet is drawn from the backing sheet by a rotating mechanism (not shown) within the crimper head 20. A second sheet is dispensed from the mid roll 124. After crimping, the first and second (used) sheets are collected by the lower roll 123. As an alternative to rollers dispensing a non-stick sheet, each metal stent may be covered in a thin, compliant protective sheath before crimping.

FIG. 1B illustrates the positioning the first sheet 125a and second sheet 124a relative to the wedges 22 and a metal stent 100 within the aperture of the crimping assembly 20. As illustrated each of the two sheets are passed between two blades 22 on opposite sides of the stent 100 and a tension T1 and T2 applied to gather up excess sheet material as the iris of the crimping assembly is reduced in size via the converging blades 22.

The dispensed sheets of non-stick material (or protective sheath) are used to avoid buildup of coating material on the crimper blades for stents coated with a therapeutic agent. The sheets 125a, 124a are replaced by a new sheet after each crimping sequence. By advancing a clean sheet after each crimp, accumulation of contaminating coating material from previously crimped stents is avoided. By using replaceable sheets, stents having different drug coatings can be crimped using the same crimping assembly without risk of contamination or buildup of coating material from prior stent crimping.

The art recognizes a variety of factors that affect a polymeric scaffold's ability to retain its structural integrity when subjected to external loadings, such as crimping and balloon expansion forces. These interactions are complex and the mechanisms of action not fully understand. According to the art, characteristics differentiating a polymeric, bio-absorbable scaffold of the type expanded to a deployed state by plastic deformation from a similarly functioning metal scaffold are many and significant. Indeed, several of the accepted analytic or empirical methods/models used to predict the behavior of metallic scaffolds tend to be unreliable, if not inappropriate, as methods/models for reliably and consiscaffoldly predicting the highly non-linear behavior of a polymeric load-bearing structure of a balloon-expandable scaffold. The models are not generally capable of providing an acceptable degree of certainty required for purposes of implanting the scaffold within a body, or predicting/anticipating the empirical data.

Moreover, it is recognized that the state of the art in medical device-related balloon fabrication, e.g., non-compliant balloons for scaffold deployment and/or angioplasty, provide only limited information about how a polymeric material might behave when used to support a lumen within a living being via plastic deformation of a network of rings interconnected by struts. In short, methods devised to improve mechanical features of an inflated, thin-walled balloon structure, most analogous to mechanical properties of a pre-loaded membrane when the balloon is inflated and supporting a lumen, simply provides little, if any insight into the behavior of a deployed polymeric scaffold. One difference, for example, is the propensity for fracture or cracks to develop in a polymer scaffold. The art recognizes the mechanical problem as too different to provide helpful insights, therefore, despite a shared similarity in class of material. At best, the balloon fabrication art provides only general guidance for one seeking to improve characteristics of a balloon-expanded, bio-absorbable polymeric scaffold.

Polymer material considered for use as a polymeric scaffold, e.g. PLLA or PLGA, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the strength needed. The scaffold also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly, bio-absorbable polymer such as PLLA or PLGA.

Processing steps performed on, and design changes made to a metal stent that have not typically raised concerns for, or required careful attention to unanticipated changes in the average mechanical properties of the material, therefore, may not also apply to a polymer scaffold due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after scaffold fabrication, e.g., crimping? As a consequence, a change to a fabrication process, post-fabrication process or even relatively minor changes to a scaffold pattern design must, generally speaking, be investigated more thoroughly than if a metallic material were used instead of the polymer. It follows, therefore, that when choosing among different polymeric scaffold designs for improvement thereof, there are far less inferences, theories, or systematic methods of discovery available, as a tool for steering one clear of unproductive paths, and towards more productive paths for improvement, than when making changes in a metal stent.

It is recognized, therefore, that, whereas inferences previously accepted in the art for stent validation or feasibility when an isotropic and ductile metallic material was used, such inferences would be inappropriate for a polymeric scaffold. A change in a polymeric scaffold pattern may affect not only the stiffness or lumen coverage of the scaffold in its deployed state supporting a lumen, but also the propensity for fractures to develop when the scaffold is crimped or being deployed. This means that, in comparison to a metallic stent, there is generally no assumption that can be made as to whether a changed scaffold pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a polymeric scaffold that is plastically deformed, both when crimped to, and when later deployed by a balloon, unfortunately, is not as easy to predict as a metal stent. Indeed, it is recognized that unexpected problems may arise in polymer scaffold fabrication steps as a result of a changed pattern that would not have necessitated any changes if the pattern was instead formed from a metal tube. In contrast to changes in a metallic stent pattern, a change in polymer scaffold pattern may necessitate other modifications in fabrication steps or post-fabrication processing, such as crimping and sterilization.

One problem encountered with a polymer scaffold is the susceptibility to damage when being crimped to a balloon. Non-uniform forces applied during a crimping process can cause irregular deformations in struts of a polymer scaffold, which can induce crack formation, and loss of strength. There is a continuing need to improve upon the crimping methods, or pre-crimping procedures used for polymer scaffold to reduce instance of crack formation or irregular strut deformation during scaffold production.

SUMMARY OF THE INVENTION

The invention provides a process and apparatus for crimping a polymer scaffold to a balloon. The polymer scaffold is expanded for placement within a lumen of the body by plastic deformation of the polymer scaffold. The crimping process used to place the scaffold on the balloon includes, in one embodiment, an initial diameter reduction followed by final crimp steps. In one respect, the invention provides both a modified crimping apparatus and a modified process for crimping a polymer scaffold to reduce damage and/or improve batch yield for polymer scaffold-catheter assemblies following the crimping phase of a production process. Modifications include modifications to a crimping blade, interior supports for a scaffold and the sequence of steps included in crimping to achieve the desired results. All of these improvements used together, or only some have been found to improve results significantly.

The invention addresses the problem of damage caused when a balloon expandable polymer scaffold is crimped to a deployment balloon. When a polymer scaffold is placed in a crimping device for metallic stents, there is frequently occurring damage done to the scaffold structure by the forces acting on the surfaces of the scaffold through crimper blades as the scaffold is crimped to the balloon. A crimping device used for metallic stents uses metallic blades and in some cases blades with hardened tips. The devices are constructed in this way to allow frequent crimping of metallic structure without pitting or deformation of the blades when deforming struts of metallic stents. Moreover, due to the relative hardness between the blades and metal stent struts, there is usually no significant structural damage to the strut of the metal stent. To the extent a blade tip bears into and forms an indentation in a metal stent strut, the stent may still perform in an acceptable manner due to the resilience and ductile properties of a metal. The polymer scaffold is much softer than a metal. As such, when a metal surface of a blade bears down on surfaces of the scaffold there is likelihood that the metal edge of the blade will permanently deform the strut by the formation of indentations, cuts or gouges in the polymer material. Unlike a metal strut, indentations raise concerns over crack propagation, especially for a brittle polymer like PLLA. Indentations are believed to occur mostly towards the end of the crimping sequence when the tips of the crimper blades are orientated more directly towards the scaffold surface.

One solution that has been proposed in the past is to enclose a drug eluting stent within a cylindrical sheath during a crimping process. However, when the diameter reduction is beyond a certain amount, a cylindrical sheath covering cannot be used. A high degree of diameter reduction (beyond the compression range for the sheath covering) of about 2.5 to 3.0 times a starting diameter causes a sheath to buckle or fold over itself during the later stages of the diameter reduction. This behavior by the sheath covering would cause more troubles than it was intended to solve.

Polymer scaffolds are also more susceptible to irregular crimping forces that result in bent, twisted, or overlapping struts. These crimping problems are due to misalignment of the scaffold within the crimper. Static charge buildup on polymer surfaces are one cause for the misalignment, e.g., as when a polymer sheet slides over a polymer scaffold surface during crimping. However, it is also believed that misalignments that would normally be tolerated when crimping a metal stent can create irregular crimping of a polymer scaffold due to the proximity of struts in a polymeric scaffold. Closely-spaced struts can cause overlapping, twisting or bending of struts as struts abut one another during a diameter reduction within the crimper. This is usually not a concern for metal stents since the struts can be made thinner, allowing for more space between struts. Also, wider spaces can be formed for metal stents since the starting diameter, before crimping, is closer to the crimped diameter. Improper crimping was also found when using a crimper that disposes polymer sheets between a scaffold and crimper blades. The polymer sheets move relative to each other as the iris reduces in size. When coming into contact with the scaffold, therefore, the sheets can induce twisting or misalignment of the scaffold within the crimper, which can lead to irregular crimping of the scaffold.

These and related problems are addressed by the invention. In one embodiment there is a method for crimping a polymer scaffold to a balloon including providing a crimping assembly for crimping the scaffold from a first diameter to a reduced second diameter, the crimping assembly including a plurality of movable blades, each blade having a hardness, a first side and a second side converging to form a tip, the tips being arranged to collectively form an iris about a rotational axis thereof, the iris defining a crimp aperture about which the movable blades are disposed; disposing a polymer material between edges of the blade tips and the scaffold surface to reduce the hardness in the edges; supporting the scaffold including inflating a balloon within the scaffold to provide interior support to the scaffold, whereby adjacent struts of the scaffold twisted irregularly by a crimper blade are supported by the balloon surface to deter one of the struts from overlapping or twisting irregularly relative to the other strut; and displacing the plurality of movable wedges from the first diameter to the reduced second diameter to reduce the diameter of the scaffold from the first scaffold diameter to a second scaffold diameter, respectively.

In another embodiment there is a method for crimping a polymer scaffold to a balloon including providing a crimping assembly; providing a polymer coating on blade tips to soften a leading edge of the blade tips; supporting the scaffold during crimping by an inflated balloon within the scaffold wherein the balloon applies a radially outward pressure to provide a stabilizing pressure to a strut displacing out of plane or twisting due to uneven crimping forces applied to the strut or near the strut; and displacing the plurality of movable blades from the first diameter to the reduced second diameter; wherein the balloon pressure is adjusted as the scaffold diameter is reduced by the tip including the leading edge such that the radially directed outward force applied on the scaffold by the balloon supports the scaffold to avoid or compensate for irregular bending or twisting of scaffold structure.

In another embodiment there is a method for crimping a polymer scaffold to a balloon including providing a crimping assembly for crimping the scaffold from a first diameter to a reduced second diameter, the crimping assembly including the plurality of movable blades, a first sheet of polymer film extending between a first and second pair of opposed blades such that a portion of the first sheet extends across an aperture formed by the iris, and a second sheet of polymer film extending between the first and second pair of opposed blades such that a portion of the second sheet also extends across the aperture; placing the scaffold on a balloon; disposing the scaffold and balloon in the aperture such that the scaffold and balloon are located between the first and second sheets; inflating the balloon; and displacing the plurality of movable blades from about the first diameter to about the reduced second diameter to reduce the diameter; wherein the balloon pressure is adjusted as the scaffold diameter is reduced by the tip such that the radially directed outward force applied on the scaffold by the balloon supports the scaffold to avoid or compensate for irregular bending or twisting of scaffold structure caused by the first and second sheets.

In another embodiment there is a method for crimping a polymer scaffold to a balloon including placing a scaffold having a first diameter on a support balloon; inflating the support balloon to a pressure for supporting and stabilizing the scaffold at the first diameter while the scaffold is being crimped; crimping the scaffold from the first diameter to a second diameter while the first balloon is supported by the support balloon; replacing the support balloon with a balloon catheter after the scaffold is reduced to the second diameter; and crimping the scaffold to a third diameter, less than the second diameter while the scaffold is supported on the balloon catheter.

In another embodiment there is an assembly for crimping a polymer scaffold to a balloon, the assembly including a plurality of movable blades, each blade having a hardness, a first side and a second side converging to form an edge, the edges arranged to collectively form an iris about a rotational axis thereof, the iris defining a crimp aperture about which the movable blades are disposed; wherein the blade edge is one or both of a polymer coated to reduce the hardness of the blade, or formed as a blunted edge wherein the blunted edge is non-symmetrically disposed about a bisecting line defining a line of action of the blade when the crimping mechanism adjusts the iris from a first to a second diameter.

In another embodiment there is a method for crimping a polymer scaffold to a balloon including placing a scaffold having a first diameter on a support balloon; the support balloon is pressurized to manipulate the orientation of the scaffold at first diameter. This orientation is used to position the metal marker beads relative to the crimp head for specific placement, with the use of a proximity sensor, e.g. a laser sensor, which is disposed within the crimp head. Lateral misplacement of the scaffold could lead to disparity between proximal and distal ends of the crimp blades. To ensure more uniformity of lengthwise crimping loads on the scaffold, thereby ensuring more uniformity in the crimped shape (particularly for longer scaffolds, e.g., 120 mm in length), the scaffold is aligned precisely within the crimper head using the alignment system.

As a further aspect of the processes described above, a scaffold may be removed from the crimp head and rotated to a selected angular position after an initial crimp, or a subsequent reduced diameter before replacing a support balloon with the catheter delivery balloon. By re-orienting the scaffold in this manner, one can establish more uniformity in the crimp profile as the scaffold diameter is reduced. For example, when using polymer sheets as described in the process in connection with FIG. 1B, the motion of the sheets relative to the blades may produce a non-uniform crimp of the scaffold about its circumference due to twisting or pulling in torsion the scaffold by the sheets (particularly when a static charge is present). Rotation of the scaffold through an angle, e.g., 90 degrees, after a crimp may help to reduce problems caused by polymer sheets.

The scope of the methods and apparatus of the invention further encompass processes that crimp the scaffolds described in US Pub. No. 2010/0004735 and US Pub. No. 2008/0275537, and the scaffolds described in U.S. application Ser. No. 12/561,971.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

In FIG. 4B the blade edge is bearing into the scaffold surface and causing an indentation to form. The blade may also further deform an already bent or twisted strut. Furthermore, the blade tip can also cut through the polymer material.

DETAILED DESCRIPTION OF EMBODIMENTS

Figure 1A:
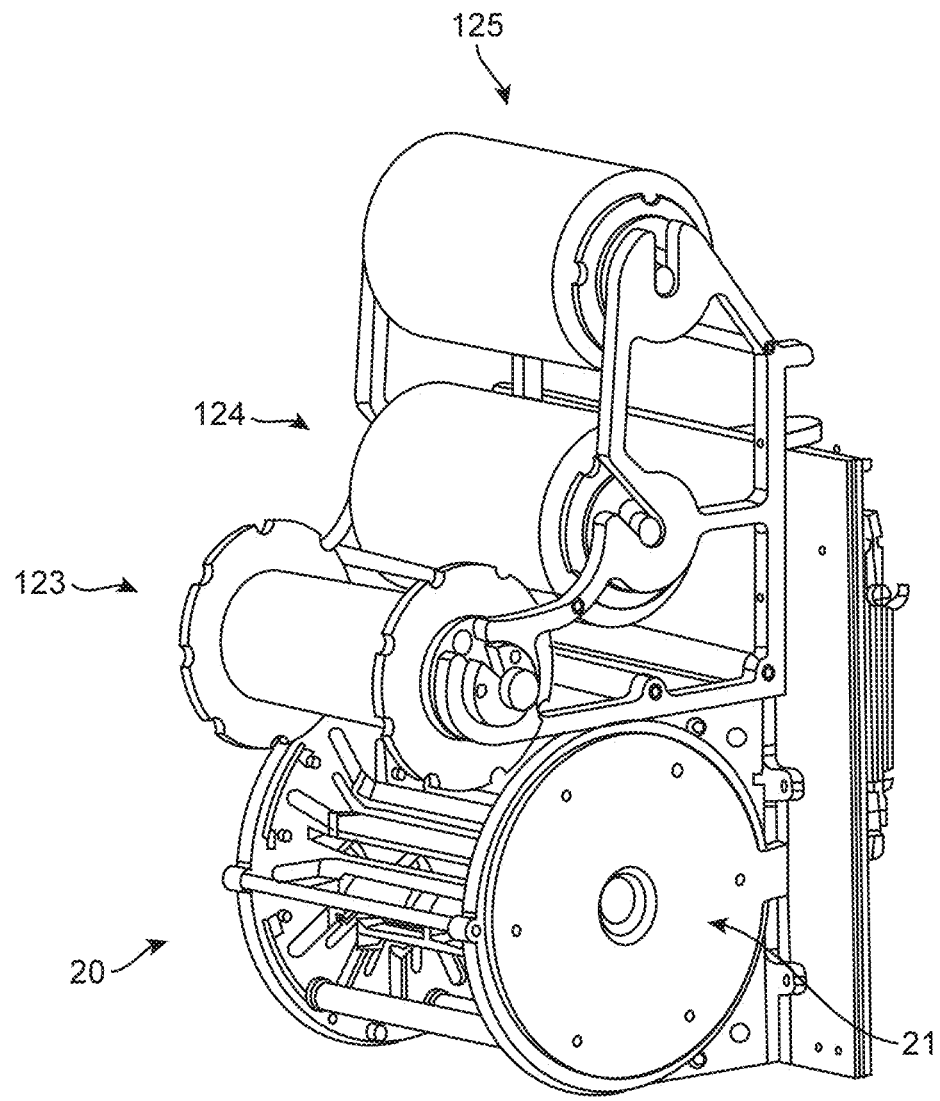
FIG. 1A shows a prior art crimping assembly utilizing opposed film sheets to provide a barrier between a drug coated stent and blades of an iris-type crimping assembly.

As discussed earlier, the invention arose out of a need to solve a problem of high rejection rates for balloon expandable polymer scaffolds crimped to a deployment balloon. Polymer scaffolds were being rejected because the structure was being irregularly deformed by the crimper, e.g., struts overlapping each other or being twisted into abnormal shapes, and because there were a high number of cracks and/or indentations formed in the scaffold. Subsequent balloon deployment, followed by accelerated life testing, cyclic and static load testing of the scaffold in its deployed state revealed that the aforementioned damage done to the scaffold was unacceptable. This damage to the scaffold when crimped resulted in a relatively high probability of failure as one or more struts fractured when the scaffold is loaded by a vessel, or the scaffold expanded improperly, thereby not properly supporting a vessel. The causes for this damage, while generally known were not easy to identify for purposes of spotting patterns or characteristic damage to the scaffold, in contrast to damage that would be caused if the crimper blades were not properly calibrated, bearings needed replacement, scaffold was not properly placed at a central portion of the crimper, etc.

As is generally known in the art, the nature of deformation of an article through externally applied forces may, in some situations, be inferred from the reaction forces applied by the article against the body, through which the external force is applied. For example, if the body applying the force to the article is programmed to enforce a displacement at a prescribed rate, monitoring the changes in the force needed to maintain the enforced displacement can give clues as to how the body is being deformed. In the case of a scaffold, an operator can set the rate for crimping and monitor the applied force. However, the known methods for instrumentation are not capable of providing the level of accuracy needed to infer how individual struts are being deformed by crimper jaws. The operator, therefore, has virtually no knowledge about how the scaffold's struts are being deformed within the crimper. The only knowledge that the operator has about how the scaffold might have been deformed when in the crimper occurs is after the scaffold is withdrawn from the crimper and visually inspected. At this point irreparable damage has occurred and the scaffold and catheter must be discarded.

The art has dealt rather extensively with improving crimping processes for metal stents. However, the assumptions made about a balloon-expandable metal stents when improving a crimping process, or problem-solving, have ignored, or underestimated significant differences between a polymer scaffold and a metal stent. First, irregular deformations of metal struts, while not desirable, seldom occur. And when they do occur, irregular deformations of metal struts are often acceptable. The same is not true of a polymer scaffold due to the inferior stress-strain characteristics of the polymer material. Second, polymer scaffolds are more susceptible to irregular deformations than metal stents due to the reduced space between polymer struts vs. metal struts (polymer struts are normally thicker and wider than metal struts, so that the polymer struts have about the same radially stiffness properties). The existing art pertaining to crimpers fails to adequately account for these differences.

Figure 2:
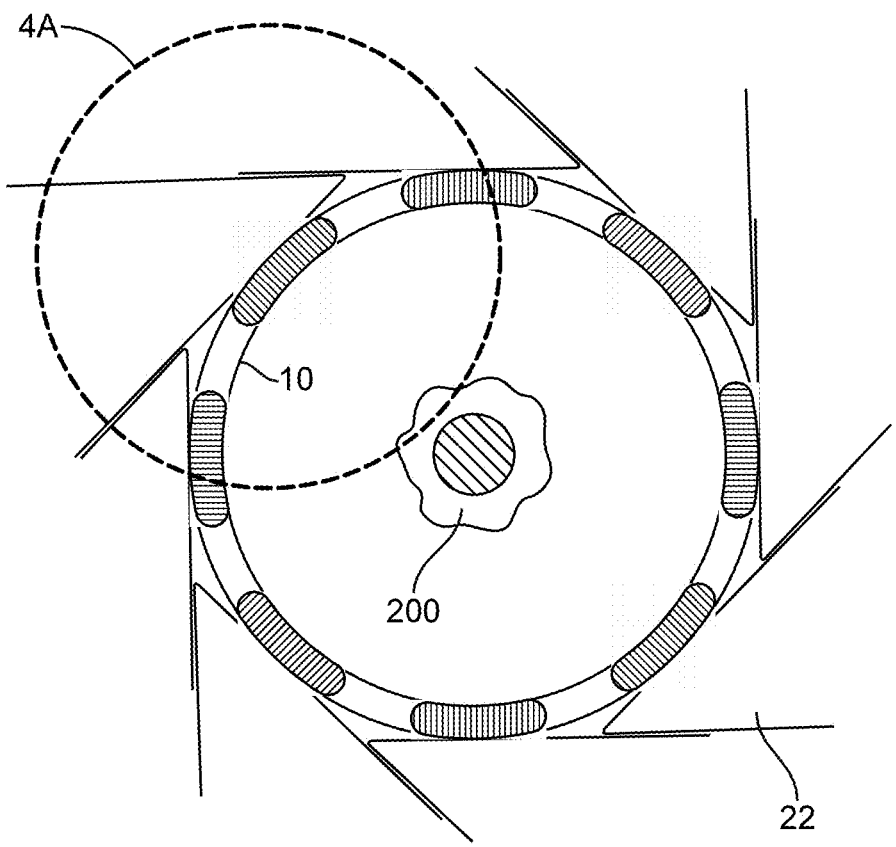
FIG. 2 shows a first cross-sectional view of blades of an iris-type crimper taken along the crimper axis when reducing a polymer scaffold diameter from a first, large diameter to a second, smaller diameter.
Figure 3:
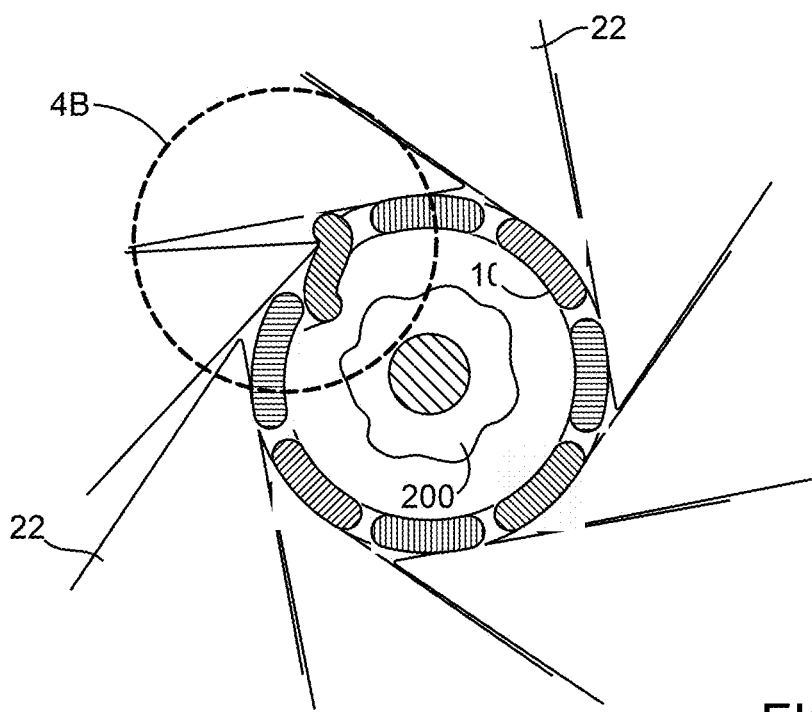
FIG. 3 shows a second cross-sectional view of blades of the iris-type crimper of FIG. 2 taken along the crimper axis when reducing the polymer scaffold diameter from a second diameter to a final crimped diameter.

FIGS. 2-4 are illustrations referred to show relationships between crimper blades and a scaffold during a crimping process when using a conventional crimping process. For simplicity, the crimper head is drawn as having only 8 blades each spanning 45 degrees. A more typical arrangement has 12 blades spanning 30 degrees each.

FIGS. 2 and 3 are cross-sectional views of a crimper head and scaffold within the aperture of the crimper head showing the orientation of the blades relative to the scaffold when the aperture forms a first diameter and second, smaller diameter, respectively. The scaffold body 10 is disposed between the blades 22. The scaffold 10 is supported on the collapsed balloon 200 of the catheter when it is placed in the crimper head. Then, as the blade edges engage the scaffold the scaffold is lifted off the balloon as shown. This setup is typical setup for a crimping sequence for a metal stent, but with the metal stent replaced by a polymer scaffold.

In FIG. 2 the blade edges are directed away from the scaffold surface so that only the more flat surface of the blade 22 abuts the scaffold surface when the aperture is at the first diameter. This means that the loading on the scaffold surface is distributed out more over the body because there is more surface-to-surface contact, thereby more likely avoiding blade indentations from forming in the scaffold. However, when the scaffold is at this large diameter problems can still occur. Since the scaffold diameter is much larger than the balloon profile, any slight misalignment, either with regards to the scaffold relative to catheter support, or the crimping blades not closing on the scaffold uniformly, can produce twisting or irregular bending as the scaffold is displaced off-center relative to the central crimping axis. The problem was found to reside with the lack of an interior, stabilizing support for the scaffold when it has the large initial diameter, e.g., 2.5 to 3 times the crimped diameter size.

In FIG. 3 the edges of the blades are directed more towards the surface of the scaffold because the blades are forming an iris that is smaller in size than in FIG. 2. In this arrangement, the relatively sharp edges of the wedge-like blades 22 are bearing down on the scaffold surface. It is in the situation that indentations, cuts and gouges causing unacceptable structural damage can occur. Moreover, if any twisting, irregular bending, or strut overlapping has begun to occur when the scaffold is at its larger diameter (FIG. 2), further twisting, bending and overlapping of struts can occur. In particular, any bending or twisting that has been initiated at the larger diameter is believed to become more pronounced or encouraged as the spacing between the struts is reduced and struts begin to abut each other. As one strut twists out of alignment, it contacts an adjacent strut which can cause the adjacent strut to be thrown out of alignment or become folded over the bent strut. As mentioned above, this problem of abutting struts is not usually present for a metal stent because either a metal stent strut is thinner or the diameter reduction required for crimping is less than for a polymer scaffold. In either case, there is more spacing between struts. Therefore, there is less chance that a misaligned strut will cause greater misalignment at smaller diameters because there is more available clearance between struts as the stent is reduced in diameter.

Figure 4A:
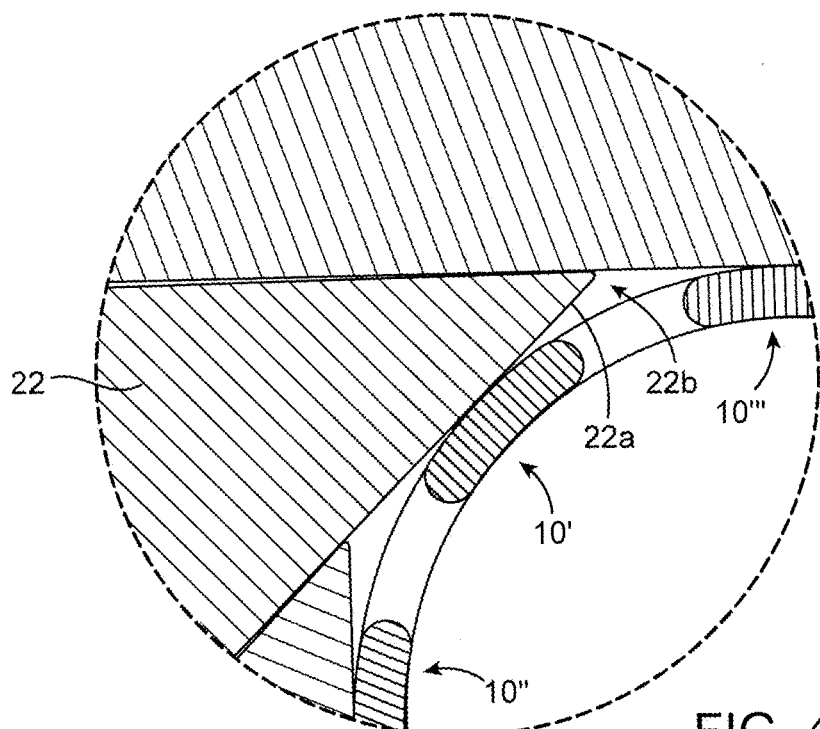
FIGS. 4A and 4B show close-up views of an individual blade of the crimper blades of FIGS. 2 and 3, respectively, as it contacts a surface of a polymer scaffold.
Figure 4B:
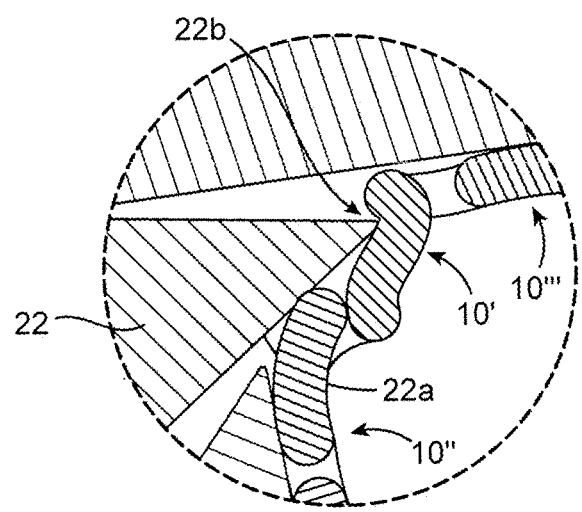

FIGS. 4A and 4B are close up views of FIGS. 2 and 3, respectively, showing the relative position of the blade edge 22b and surface 22a away from the edge 22b relative to the surface of the scaffold 10. FIG. 4B depicts a deformation, tearing or gouging being formed in the scaffold structure as a result of the edge 22b bearing down upon the scaffold. This situation is believed to occur when an edge of the blade catches the edge of a scaffold strut, such as a strut that was previously deformed or twisted, even slightly, out of position so that the blade edge 22b catches it. As depicted, strut or crown 10' has been twisted and through abutment with strut 10" results in the struts or crowns overlapping each other. Once this interaction between struts begins and the diameter is reduced further, the problem can become worse and worse until the scaffold becomes unusable. As a result, both the scaffold and catheter supporting the scaffold is discarded.

As will be appreciated, it is very difficult to know the exact mechanism of action, or sequence of events leading to the situation depicted in FIG. 4B or that shown in FIGS. 11-12 and 14, for two reasons. First, one cannot generally visually inspect the interaction between blades and a scaffold. One can only inspect what the crimped shape looks like after the scaffold is removed from the crimper. Second, a polymer scaffold is typically transparent, or at best semi-opaque. When crimped to a transparent balloon, it can therefore be extremely difficult to determine the exact nature or extent of cuts or indentations across the body of the scaffold in order to spot a pattern or characteristic damage.

It was also discovered that polymer scaffolds are susceptible to damage if they have a slight misalignment with the blades of the crimping assembly of crimper. A "slight" misalignment means a misalignment that the art has tolerated in the past and assumed were present but not capable of significantly effecting how a metal stent would be deformed by the crimper as compared to the same stent when perfectly aligned with and coming into contact with the blades of the crimper. Such misalignment tolerance is understood by reference to information available from a manufacturer of a commercially available crimping device. One type of misalignment of crimper blades believed to cause unacceptable damage to polymer scaffold would be when one blade is not maintained flush with an adjacent blade, such that when the iris diameter is reduced a sharp leading edge is exposed. This sharp edge can then tear into, or cut across a polymer strut, e.g., resulting in the damage shown in FIGS. 12A-12B.

Figure 12B:
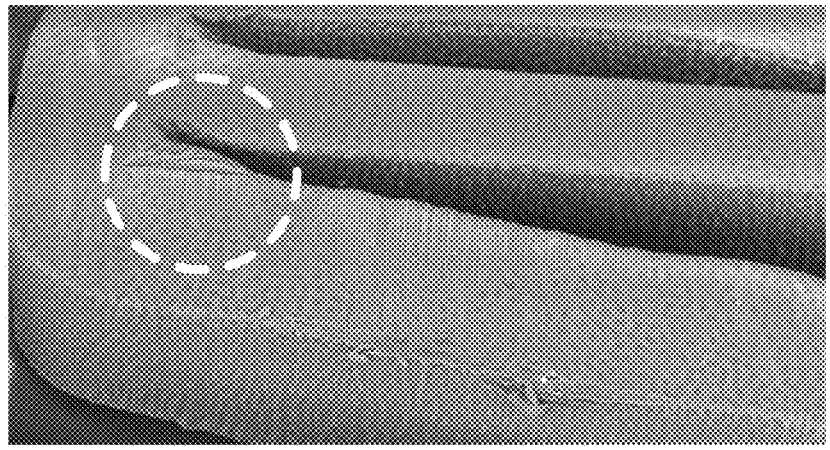
FIGS. 12A-12B show cuts, indentations and gouges formed in the polymer material for a polymer scaffold having an as-deployed strut pattern as depicted in FIG. 5 when a conventional crimping process is used to crimp the scaffold to a balloon.
Figure 12A:
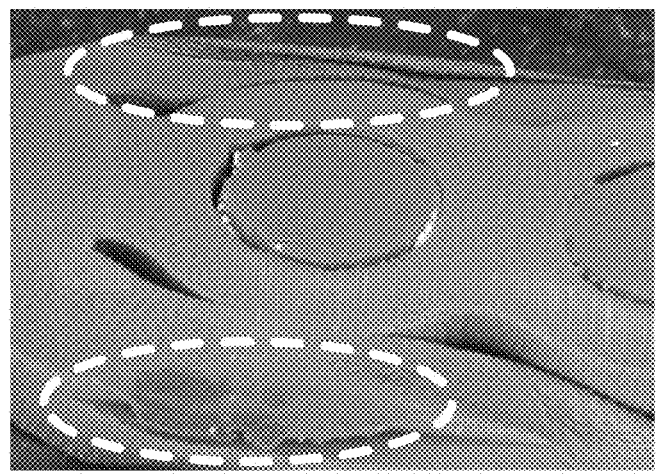
Figure 15:
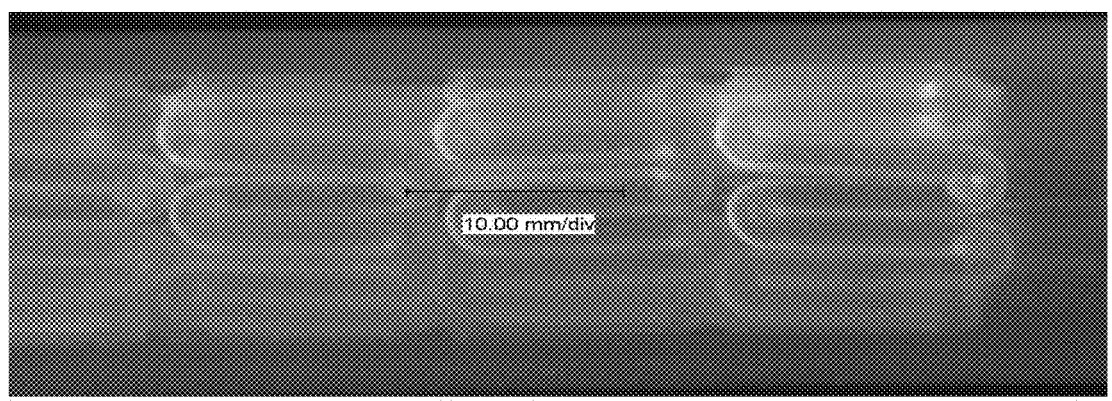
FIG. 15 shows a crimped polymer scaffold having an as-deployed strut pattern as depicted in FIG. 10 when processes according to the invention are used.
Figure 13:
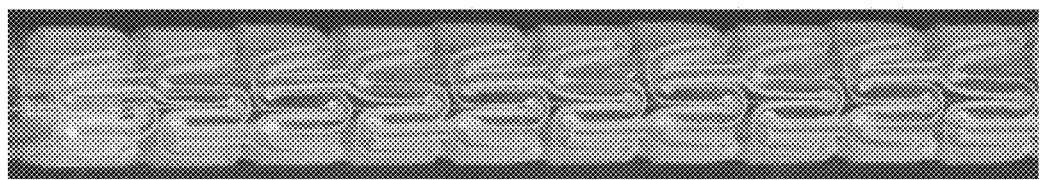
FIG. 13 shows a crimped polymer scaffold having an as-deployed strut pattern as depicted in FIG. 5 when processes according to the invention are used.

FIGS. 11-12 and 14 are photographs showing damage to polymer scaffold using a known crimping process for metal stents. FIGS. 13 and 15 show, however, a marked improvement in crimping when processes according to the disclosure are used in place of the known crimping process. FIGS. 11-13 are photographs for the scaffold depicted in FIG. 5. FIGS. 14-15 are photographs for the scaffold depicted in FIG. 10.

Figure 11B:
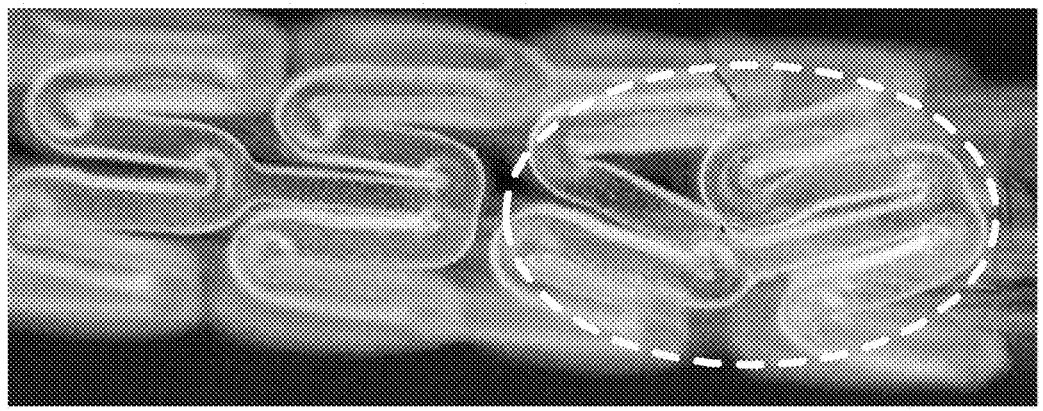
FIGS. 11A-11B show pinching and bending of strut sections for a polymer scaffold having an as-deployed strut pattern as depicted in FIG. 5 when a conventional crimping process is used to crimp the scaffold to a balloon.
Figure 11A:
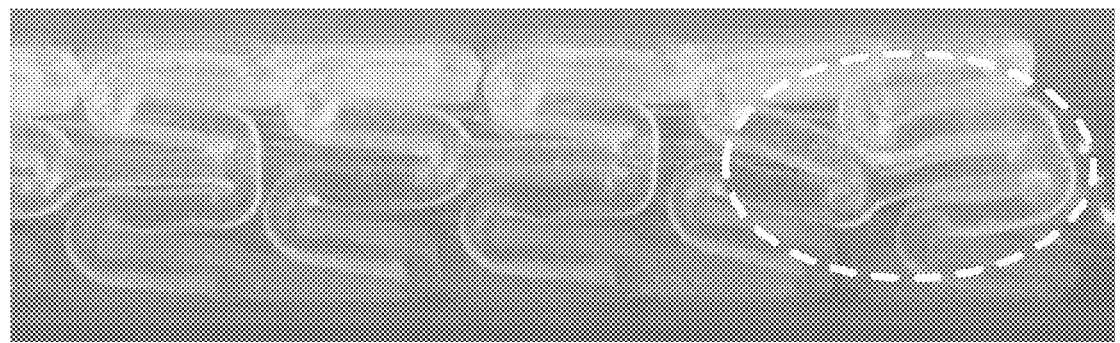

FIGS. 11A-11B show two types of defects in a crimped scaffold. FIG. 11A shows that the linking element connected to the crown is bent. This bent "Y" section of the scaffold caused the crimped scaffold to be rejected. The region where the bending has occurred is a known high stress area where fracture is more likely to occur in the deployed scaffold. For this reason, the scaffold is rejected. Similarly, FIG. 11B shows a defect that will cause this scaffold to be rejected as well. The defect here is, not only, a bent "Y" section, but also a pinching of the crown. As can be seen in this photograph, an upper crown is pressing against the lower crown forming the "Y". The result is the struts are squeezed together beyond their designed bending ranges. Balloon expansion from this abnormal shape, therefore, raises concerns over loss in stiffness or fracture toughness for the scaffold, in this area or areas nearby. FIGS. 12A and 12B are scanning electron microscope images showing abrasions, cuts, gouges and indentations in the scaffold due to the knife-like edge of the crimper blade bearing down on the scaffold. This damage to the scaffold is likewise unacceptable and results in the scaffold being rejected. When using a conventional crimper head, damage like that shown in both FIGS. 11 and 12 are likely present in the crimped scaffold. Indeed, before the invention there was a near 0% yield for scaffold that were devoid of the damages depicted in FIGS. 11-12.

Figure 10:
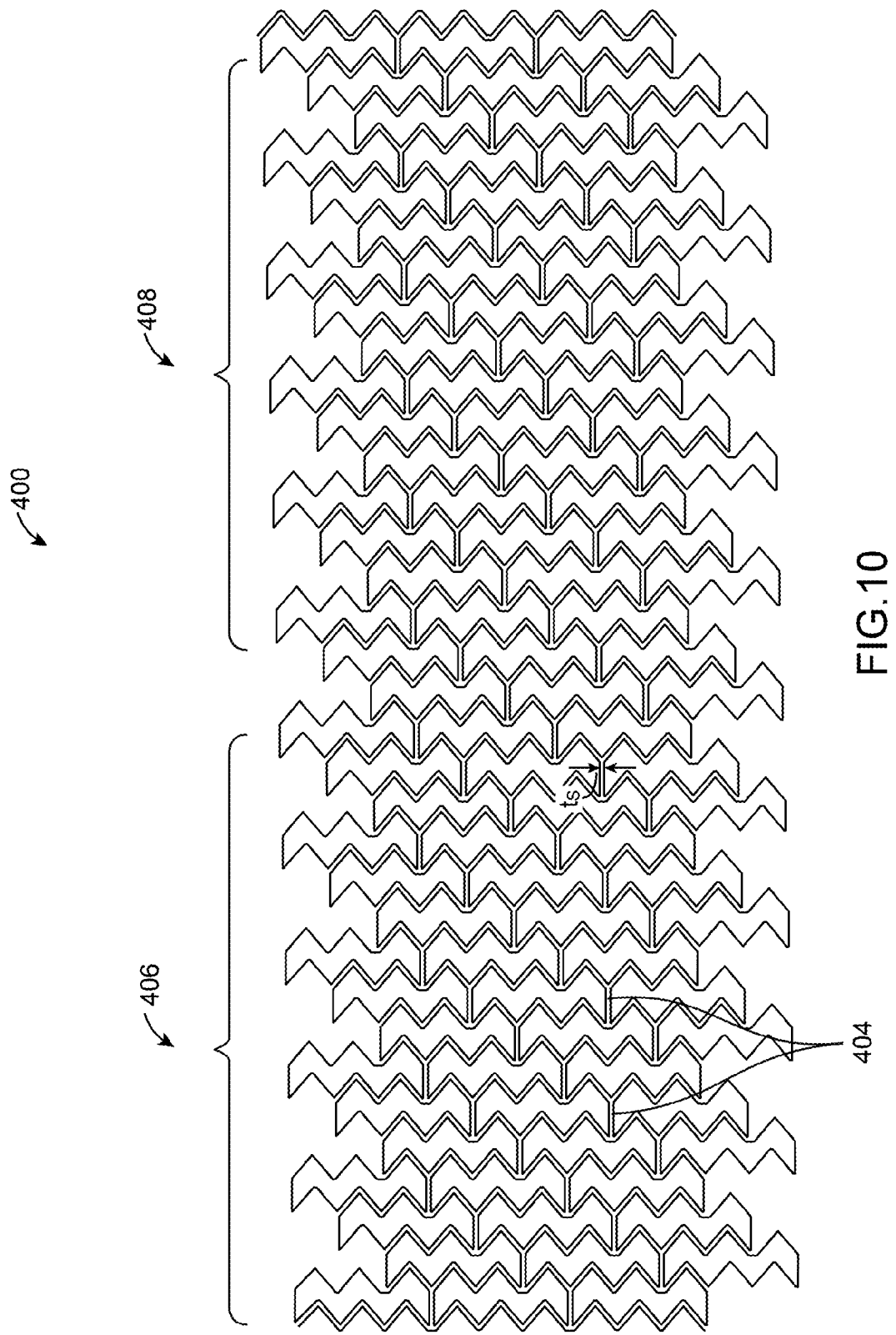
FIG. 10 is a third disclosure of a pattern for a polymer scaffold crimped to a balloon according to the invention
Figure 14A:
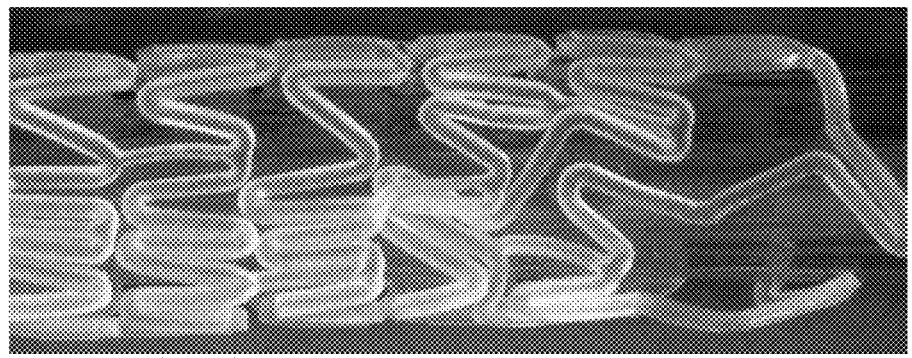
FIG. 14A-14C show irregularities and damages to a polymer scaffold having an as-deployed strut pattern as depicted in FIG. 10 when a conventional crimping process is used to crimp the scaffold to a balloon.
Figure 14B:
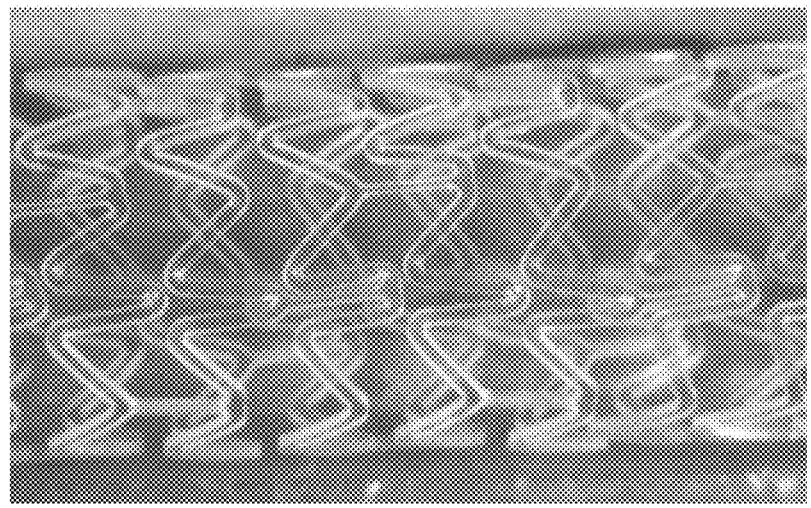
Figure 14C:
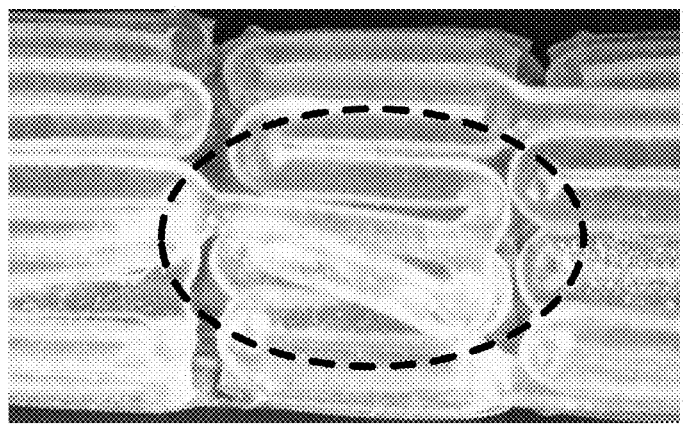

FIGS. 14A-14C depicts damage observed for the scaffold described in FIG. 10. As can be readily seen, in FIG. 14A the scaffold exhibits severe irregularity, e.g., bent and even flipped struts, overlapping struts and pinched struts. FIG. 14B, while not showing the severity in bending and twisting as in the case of FIG. 14A, nonetheless is also an unacceptable crimping for a scaffold since Y or W elements at one circumferential station are being crimped at a different rate from another circumferential station. It is believed that if this scaffold were crimped further, overlapping, flipping or similar undesired deformation of the scaffold will occur. FIG. 14C shows a close-up of overlapping struts. This scaffold, as was the case of the scaffold depicted in FIGS. 14A-14B, was rejected. The overlapping struts in this section can result in improper deployment, as well as significant loss in stiffness and fracture toughness.

The inventors discovered, unexpectedly, that if "slight" misalignments were removed, or substantially removed, when crimping a polymer scaffold, there can be significant reductions in the irregular deformations of scaffold struts that are sufficient to cause irreparable damage to a polymer scaffold, e.g., a PLLA scaffold. A misalignment refers to either the scaffold bore axis not aligning with the crimper central axis or the scaffold not aligning properly with the blades of the crimping device axis as the iris is being closed onto the scaffold. One may view the two as global verses local misalignment. Better alignment of the scaffold body and better support of the scaffold relative to the moving blades within the crimper was found to yield improved results, particularly when the scaffold requires a significant diameter reduction and a high retention force.

Again, it should be mentioned that a polymer scaffold, and in particular a misaligned polymer scaffold is more susceptible to damage within a crimper than a corresponding metal stent. A polymer scaffold that has a "slight" misalignment within the crimper has a far greater chance of becoming damaged than a metal stent. Of course, the need to avoid twisting, bending or indentations in struts of metal stents when in a crimper is known. However, unlike metal stents, which are far more tolerant to local irregular or non-uniform forces acting on struts through blade edges, a polymer scaffold surface has a much lower hardness than a metal stent surface. Therefore, the polymer scaffold is more susceptible to local damage by the crimper blades. Moreover, due to the proximity of struts to each other (as required since thicker and wider struts are needed to provide equivalent stiffness to a metal stent), there is a greater chance of abutting struts which leads to out of plane twisting and overlapping scaffold structure in the crimped state. The affect of irregular or non-uniform crimping forces on a polymer scaffold are therefore more severe than in the case of a metal stent. The differences are most clearly evident in the instances of cracking and/or fracture in deployed polymer scaffolds that exhibit irregular twisting or bending and indentions.

Crimping a polymer scaffold in the manner illustrated in FIGS. 2 and 3 was found to be inappropriate for these reasons. Scaffolds crimped in this manner are often damaged and of no use. In one example using a crimping device and crimping process for metal stents the yield was near 0%. When aspects of the invention were employed, the yield was increased to 80%.

Figure 9:
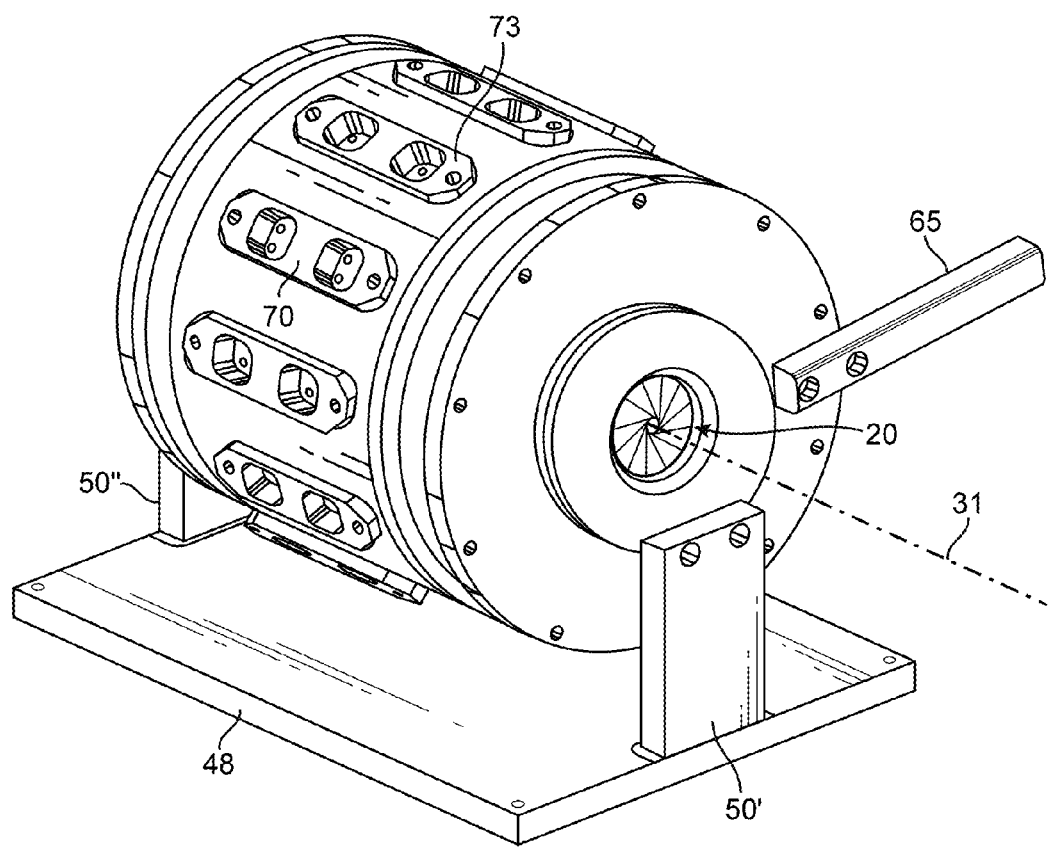
FIG. 9 shows a perspective view of a crimping device having a plurality of movable blades that form an iris for crimping.

A crimping assembly according to the disclosure may adopt an iris-type actuating mechanism alluded to above, an example of which is described in U.S. Pat. No. 7,389,670, which disclosure, including all drawings, is fully incorporated herein for all purposes. FIG. 9 is a perspective view of such a crimping assembly 20 incorporating a crimping mechanism that includes a collection of blades, e.g., twelve 30 degree blades, that articulate circumferentially and radially where each blade is articulated radially and circumferentially in unison with the other blades by a two axis linking mechanism (combined radial and circumferential motion for each blade). The assembly thus includes a plurality of blades arranged to form an aperture 21 with variable diameter. The crimping assembly 20 includes a base 48, supports 50' and 50" and an arm 65 for causing the blades to move inwards or outwards for reducing or enlarging, respectively, the aperture 21 formed by the iris. The central axis for the crimping blades, or crimping axis for the assembly is drawn as axis 31 in FIG. 9.

The problems previously described above with existing crimper assemblies for polymer scaffolds were addressed by methods including (1) modifying the contacting surfaces of the crimper blades with the scaffold, (2) supporting the scaffold from the inside using balloon pressure. Embodiments of these aspects of the disclosure are provided.

Figure 1B:
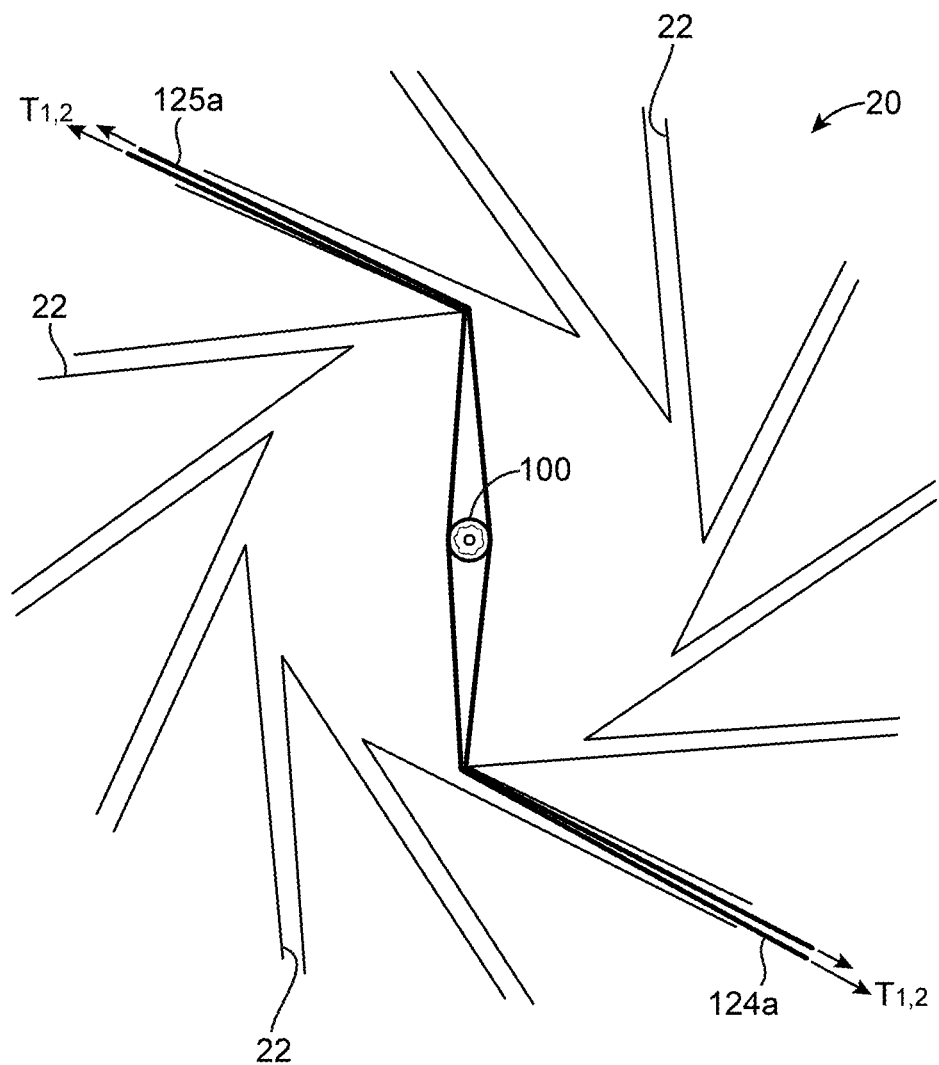
FIG. 1B is a cross-sectional view taken along a crimping axis of the iris-type crimping assembly of FIG. 1A. This drawing illustrates the use of tensioned polymeric sheets used to maintain a clean surface on the crimper blades when metal stents carrying different drug-polymer coatings are crimped to a balloon.

In one embodiment a polymer scaffold is crimped using a crimper assembly that supplies sheets of polymer film between the scaffold and crimper blades. An example of this type of crimping assembly is illustrated in FIGS. 1A and 1B. It was found that the polymer sheet also helped to reduce indentations in scaffold surfaces since the polymer sheets effectively made the blade surfaces more compliant. However, disposing a polymer material between the blades and scaffold surface was not enough to reduce damage to the polymer scaffold. An unacceptably high number of damaged scaffolds still resulted when the crimped scaffold was removed from the crimper of FIGS. 1A-1B.

It was believed that the sheets of material, while reducing indentations due to the effective reduction in compliance of the blades, also imposed twisting forces on the scaffold, which promoted irregular bending or twisting in the struts of the scaffold when the blades bore down on the scaffold surface. While not wishing to be tied to any particular theory, it is thought that by introducing sheets of material between the scaffold and blades, the tension on the sheets, combined with the movement of the blades relative to the sheets may have lead to the undesirable consequence of increasing the twisting of the unsupported scaffold body as the diameter was reduced, which exacerbated, in some respects, the irregular crimping observed. In another sense, it was believed that the irregular deformations of struts caused by individual blades could not be reduced enough to increase the yield of usable scaffold-catheter assemblies when only a more compliant surface was introduced by way of the polymer sheets. In an attempt to produce more uniform crimping and thus more acceptable yields, an interior support for the scaffold was introduced during an initial diameter reduction, e.g., reducing the scaffold diameter to about ½ its starting diameter. An inflated balloon was used to support the scaffold. An inflated balloon was also employed when the scaffold was reduced down to its final crimped diameter. It is not known, for certain, whether the improved yield of scaffold-catheter assemblies was due solely to, or mostly to the use of a balloon support during the initial diameter reduction or the combination of inflated balloons during several incremental crimping steps. As explained above, the precise cause and effect resulting in damaged scaffold structure is not easily determinable due to complex nature of the inelastic deformation of the polymer material and inability to closer inspect each phase of the crimping sequence. Nevertheless, testing reveals that when balloon pressure provides support for the scaffold, the yield of scaffold-catheter assemblies improves dramatically.

More local support for individual struts when the scaffold nears its final crimped diameter is believed to add some measure of support for struts predisposed to twist or overlap with adjacent struts (a strut predisposed to twist or overlap with other struts refers to a strut that was previously slightly bent or twisted out of plane when the scaffold was at a larger diameter. As discussed earlier, due to the proximity of struts for a polymer scaffold, as opposed to a metal stent, there is therefore a greater likelihood of bending, twisting or overlap as struts abut each other). In essence, balloon pressure is believed to provide a beneficial reacting pressure upon the luminal side of the strut, which can serve to limit a strut's potential to overlap or twist irregularly when a blade edge imparts a higher degree of force to a strut than the blade applied during an earlier crimping step.

Balloon pressure helps to stabilize the scaffold during the initial phases of the crimping sequence. In one example, the scaffold is reduced from an over-deployed or deployed diameter to a diameter that about 2.5 to 3 times smaller in size. When at the deployed or over-deployed diameter, there is little stabilizing support for the scaffold since its diameter is much larger than the deflated balloon catheter upon which the scaffold sits. As such, any initial non-uniform applied crimping force, or misalignment, e.g., due to a residual static charge on the polymer surface, can initiate irregular bending that becomes more pronounced when the scaffold diameter is reduced further. Friction between the blades and the scaffold surface, or residual static charge or static charge buildup induced by sliding polymer surfaces are also suspect causes of this irregular deformation of the scaffold. When the balloon was inflated to support the scaffold from the interior, it was discovered that the irregular bending and twisting of struts were reduced substantially. The scaffold was more able to maintain a proper orientation with respective to the crimper axis. The uniform pressure applied by the balloon tended to balance-out any non-uniformity in the applied crimping force.

Additional crimp refinements were employed by the inventors in an effort to improve scaffold-catheter assembly yield. First, polymer surfaces within the crimper head, whether in the form of polymer sheets or coatings disposed on the blades (as discussed in greater detail, below), are deionized prior to crimping to avoid static charge buildup. Second, scaffold temperature is raised to near the glass transition temperature of the polymer to reduce instances of crack formation during crimping (as well as to increase balloon retention), but without affecting the deployed structure's strength and stiffness profile. These additional improvements to polymer scaffold crimping processes are discussed in more detail in U.S. application Ser. No. 12/776,317 and U.S. application Ser. No. 12/772,116. These applications share a common inventor and assignee with the present application.

Figure 5:
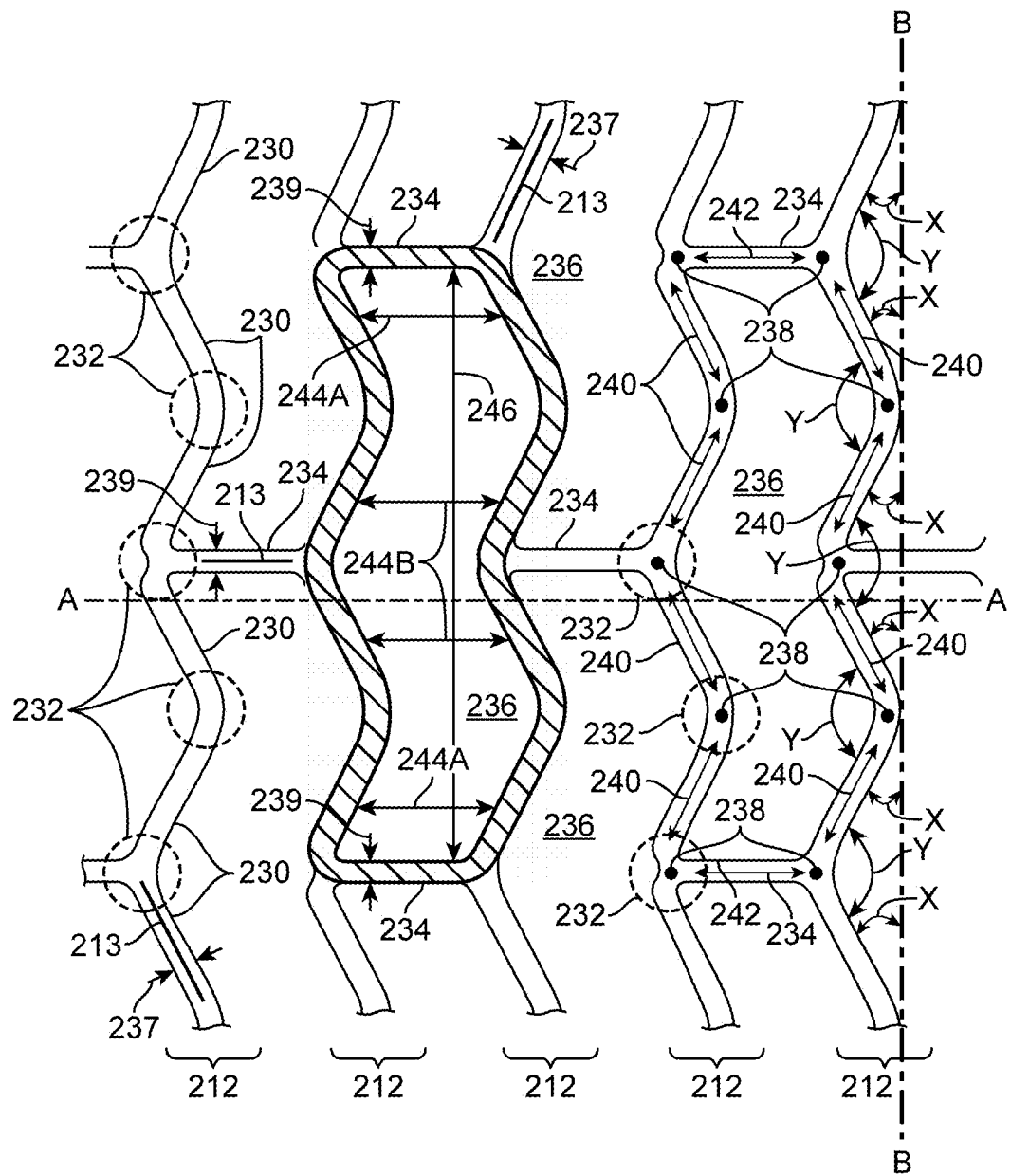
FIG. 5 is a first disclosure of a pattern for a polymer scaffold crimped to a balloon according to the invention.
Figure 6:
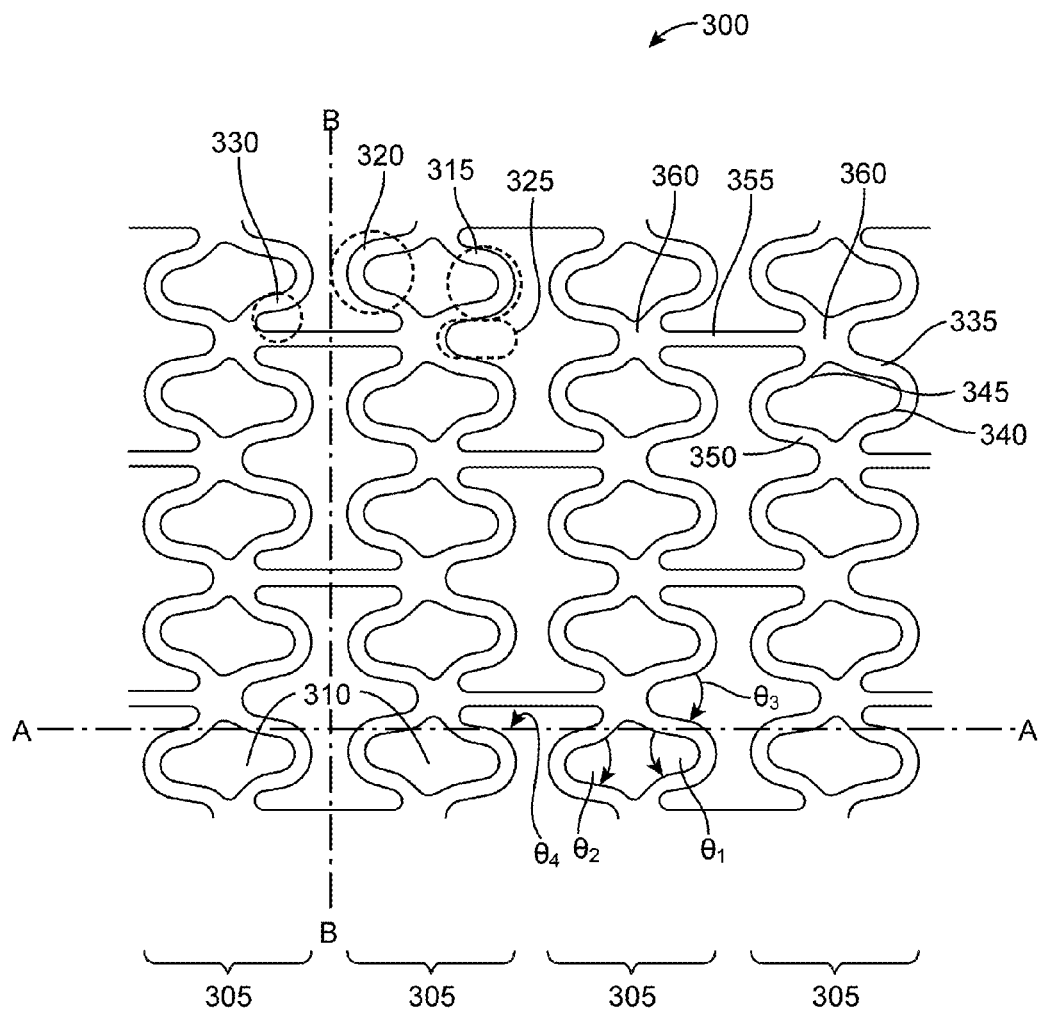
FIG. 6 is a second disclosure of a pattern for a polymer scaffold crimped to a balloon according to the invention.

Examples of crimping sequences/protocols for reducing damage to a polymer scaffold will now be discussed. In these examples, the scaffold was formed from a radially expanded tube of PLLA. The scaffold had a strut pattern as shown in FIG. 5, 6 and FIG. 10. An iris crimper having similar actuating characteristics to the crimping assembly described in connection with FIG. 9 was used to pre-crimp and final crimp the scaffold to the balloon.

A crimping process for a polymer scaffold having the scaffold pattern of structural rings, struts and linking elements shown in FIG. 5, 6 or 10 may proceed as follows. In preparation for the initial diameter reduction, the scaffold is placed on a balloon and deionized, the polymer sheets disposed within the crimping aperture 21 are deionized, and the scaffold is placed with the crimper 20. The temperature of the crimper blades are raised to, or to about 48° C. and allowed to stabilize at that temperature. The radiant and convective heat from the blades is relied on to raise the temperature of the scaffold when the scaffold is in the crimper. Hot air may also be introduced to raise the scaffold temperature.

Unlike a metal stent, a polymer scaffold of the type illustrated in FIG. 5, 6 or 10 requires an initial diameter reduction or pre-crimp, a re-alignment or alignment check with balloon markers, followed by a final crimp procedure due to the initial large diameter of the polymer scaffold, which large diameter may correspond to a deployed or over deployed diameter for the scaffold. A polymer scaffold is formed in this way so that it can possess the polymer chain alignment most optimal for providing high stiffness and low recoil in the deployed state. This configuration, however, also makes the crimping process more challenging because there is large diameter reduction needed (metal stents, in contrast, due not require this form of assembly due to the difference in material properties. Metal stents may be fabricated at a reduced diameter, which makes it far easier to crimp the metal stent to a balloon since the starting diameter is closer to the crimped diameter). In one embodiment, a scaffold is reduced from a starting diameter of about 0.136 in to a crimped diameter of about 0.052 in. In another embodiment, a scaffold is reduced form a starting diameter of about 9 mm to a crimped diameter of between about 2 and 3 mm.

In the embodiments, an anti-static filtered air gun is used to deionize the scaffold before and/or during pre-crimping. Before pre-crimp, the anti-static air gun is passed over the scaffold front to back to remove static charges on the scaffold. In one case, the anti-static filtered air gun is applied for 10 seconds to 1 minute along the scaffold. In another embodiment, the air gun deionizes the scaffold during pre-crimping. The anti-static filtered air gun is applied for 10 seconds to 1 minute along the scaffold.

EXAMPLES

The crimping sequence for a 3.0×18 mm PLLA scaffold having the pattern illustrated in FIG. 5 is illustrated as an example. The initial pre-crimp moves the blades forming the iris from a starting diameter of 0.136 in to a diameter of 0.083 in where it remains for a 30 second dwell. This is stage 1. During this stage balloon pressure may be applied to stabilize the scaffold, in an amount of about 2 to 15 psi. The scaffold and balloon upon which the scaffold rests is then removed from the crimper and the alignment with balloon markers verified. The diameter reduction to 0.082 in loosely secures the scaffold to the balloon so that it can hold its place but is still capable of being adjusted relative to balloon markers. The scaffold is returned to the crimper.

Stage 2 of the crimping sequence moves the blades forming the iris from to a 0.068 in and is held for 15 seconds. During this stage, the balloon is inflated to about 17 to 100 psi. After this stage is complete, the balloon is deflated and the iris opened to allow the catheter to be removed. The scaffold receives a final alignment to the balloon markers. The scaffold and balloon are placed back into the crimper. Stage 3 reduces the diameter to 0.070 in with a 10 second dwell. During this stage 3, the balloon is inflated to about 17 to 100 psi. Once complete, the machine moves to Stage 4, where the balloon pressure is reduced to lower than about 15 psi and iris reduced to 0.047 in and held for a final 200 second dwell. When this fourth and final stage is complete, the iris is opened and the catheter and scaffold removed. The scaffold is retained on the balloon and immediately placed into a sheath minimize recoil in the polymer scaffold.

A balloon pressure during diameter reduction may be selected to provide support for the scaffold without imposing excessive stresses on the balloon material. Alternatively, a compliant and expendable support balloon held at a constant pressure may be used during the initial diameter reduction, as in the case of the scaffold of FIG. 10. In some embodiments, the balloon pressure may be adjusted by a controlled release of gas pressure as the scaffold diameter is decreased. In other embodiments, the balloon pressure may be increased after an incremental diameter reduction is made, during a dwell period. By increasing balloon pressure immediately after an incremental crimp, any irregular deformations can be adjusted by supporting balloon pressure, which provides a uniform pressure to the inner surfaces of the scaffold to compensate for any tendency for a strut to irregular deformation. For example, a strut that was deformed inwardly can be pushed back into position when the balloon is inflated.

In another embodiment a scaffold reduced in diameter from about 9 mm to about 2-3 mm has a 120 mm length. For this scaffold the crimping sequence may proceed as follows using a crimping station such as a crimping station described in U.S. application Ser. No. 12/831,878.

In a first and second example, a crimp process for the scaffold depicted in FIG. 9 is crimped at a temperature of about 48 degrees Celsius for PLLA scaffold material. For PLGA the temperature may be lower. The scaffold temperature is raised via convection and radiation from the heated crimper blades.

The 9 mm ID scaffold is placed on a 9-10 mm support balloon. This balloon is inflated through a sidearm of the balloon with 40-70 psi air to create a balloon OD of 8 mm. Keep the support balloon pressurized. Place this scaffold-balloon assembly on the loading carriage. Push the carriage forward until the assembly is in the center of the crimp head.

First example of a crimp process following the scaffold-balloon placed in crimp head:

Stage 1—crimp head closes to 0.314" at a speed of 0.5 inches per second (in/s) then immediately go to Stage 2.

Stage 2—crimp head closes to 0.300" at a speed of 0.005 in/s and dwells for 30 seconds.

Stage 3—crimp head closes to 0.270" at a speed of 0.005 in/s and dwells for 30 seconds. Turn stopcock to release pressure from the inflated support balloon catheter.

Stage 4—crimp head closes to 0.240" at a speed of 0.005 in/s and dwells for 30 seconds.

Stage 5—crimp head closes to 0.200" at a speed of 0.005 in/s and dwells for 30 seconds.

Stage 6—crimp head closes to 0.160" at a speed of 0.005 in/s and dwells for 30 seconds. Activate pressurization mode of crimping station to inflate the support balloon with 50 psi to align any misaligned struts between Stage 3 and Stage 5. After dwelling for 30 seconds the crimp head opens, remove the scaffold/support balloon from the crimp head. Remove partially crimped scaffold and place it on the balloon of the balloon catheter ("FG balloon catheter"). Insert this assembly back into the center of the crimp head. Reactivate the crimper.

Stage 7—crimp head closes to 0.160" at a speed of 0.25 in/s and dwells for 30 seconds.

Stage 8—crimp head closes to 0.130" at a speed of 0.005 in/s and dwells for 50 seconds. Activate pressurization mode to inflate the FG balloon catheter 50 psi to create pillowing effect to improve scaffold retention and dwell for 50 seconds. Deactivate pressurization mode after 50 seconds have elapsed.

Stage 9—crimp head closes to 0.074" at a speed of 0.005 in/s and dwells for 150 seconds.

Remove finished scaffold-catheter assembly from crimp head and immediately place restraining sheath over scaffold to limit recoil.

Second example of a crimp process following the scaffold-balloon placed in crimp head.

Stage 1—crimp head closes to 0.314" at a speed of 0.5 inches per second (in/s) then immediately go to Stage 2.

Stage 2—crimp head closes to 0.160" at a speed of 0.005 in/s and dwells for 30 seconds. During this stage a relief valve releases pressure from the pressurized support balloon catheter to prevent balloon rupture. After dwelling for 30 seconds the crimp head opens, remove the scaffold/support balloon from the crimp head. Remove partially crimped scaffold and place it on a FG balloon catheter. Insert the subassembly back into the center of the crimp head. Reactivate crimper.

Stage 3—crimp head closes to 0.130" at a speed of 0.005 in/s and dwells for 50 seconds. Activate pressurization mode to inflate the FG balloon catheter to 50 psi to create pillowing effect to improve scaffold retention and dwell for 50 seconds. Deactivate pressurization mode after 50 seconds have elapsed.

Stage 4—crimp head closes to 0.074" at a speed of 0.005 in/s and dwells for 150 seconds.

Remove finished scaffold-catheter assembly from crimp head and immediately place restraining sheath over the scaffold to limit recoil.

In yet another alternative to these crimping processes, in a third example the scaffold is rotated about its axis while supported on the support or temporary balloon between intermediate crimping stages. Thus, after an initial crimp, the scaffold and support balloon are removed from the crimper head and the scaffold is rotated, e.g., about 45 degrees about its axis, then a second crimp is performed. The same step may be performed several times until the diameter is reached in which the temporary balloon is replaced by the balloon catheter. In another example, the rotation may be less than 30 degrees, or the angle extending between adjacent "Y" shape elements. The angle of rotation may also be the ½ angle between Y-shaped elements to compensate for a non-uniform crimping such as that depicted in FIG. 14B.

In other embodiments a polymer coating is applied to edges of blades, rather than using tensioned polymer sheets as in FIG. 1B. The effect is to reduce the hardness of the blade surfaces that contacts the polymer scaffold, or to cause the crimper blade loading of the scaffold struts to by more widely distributed over the surface. In another sense, the objective is to make the blade edge softer so that its hardness is closer to that of the relatively soft polymer surface. In doing so, the blade forces (especially at or near the blade edge) will be distributed over a greater portion of the surface of the scaffold (since the surface is made more soft) which should reduce indentations on the scaffold surface, especially when the iris diameter moves to the final crimp diameter (FIG. 3). Hardness is meant to refer to the resistance of a surface to permanent shape change when a force is applied. For present purposes, hardness refers to indentation hardness, or the ability to resist a permanent indentation from forming. Since it is not desired to change properties of the polymer scaffold so as to affect its hardness, the hardness of the blade is changed, i.e., it is made softer, by applying a polymer coating of suitable hardness to the blade edge.

On the one hand, one may wish to match the hardness of the coated blade to the scaffold surface, which is intended to mean the "effective" hardness of the blade, i.e., the hardness of the coated surface that comes into contact with the scaffold surface. This arrangement would perhaps be most ideal from the standpoint of avoiding indentations in the scaffold while ensuring the blades are capable of deforming the scaffold struts in the intended manner. On the other hand, reducing blade hardness to this degree would require more frequent maintenance of the blades as the coated blade edge would become deformed or removed from the blades relatively often (depending on the material used) following a production crimping run. Reducing blade hardness so that it is about at the hardness of the scaffold may also not be desired when crimping at elevated temperatures.

For example, to reduce the blade hardness to the hardness of the scaffold there may be a relatively thick coating requirement, or a polymer material may be needed that has a relatively low heat transfer coefficient. In either case, the polymer coating used to match hardness may make it difficult to effectively or efficiently conduct heat from the blades to the scaffold in those cases where the scaffold is heated by heat conducted and radiated from the metal blades.

The polymer coating may be polyurethane or any other relatively elastic polymer material. The coating thickness applied to blades may range from about 100 to 150 microns, depending on the material used. The thickness of the coating may be selected to make the edge of the crimper blades more soft but without causing thermal insulation problems. For example, a polymer coating thickness may be maintained at a constant thickness, or having a tapered thickness so that damages caused by sharp edges are reduced yet the scaffold can be efficiently heated to a desired crimping temperature by way of blade radiation/conduction.

According to one embodiment, a scaffold inserted within a crimper head exposed to crimper blades will obtain a temperature at about the glass transition temperature of the polymer, and more preferably between 5 or 10 degrees below the glass transition temperature without additional heating sources being required for a tapered polymer thickness over the blade edge contact length, or less than this length, with a maximum thickness being at or near the sharp tip being between about 100 and 150 microns. As alluded to above, if the coating is too thick or disposed over much of the tip of the blade, then heat convection from the blades to the scaffold may become impaired which makes scaffold heating through the crimp blades infeasible, or impractical for batch or production crimping. In addition, or alternatively, the hardness of the edge modified by the coating to reduce indentations from forming in the scaffold may also make the blade more susceptible to deformation (since the surface is softened), which may necessitate frequent maintenance of the polymer coated blades.

The polymer coating may further, or in addition to, be evenly applied over the edge of the blade, or applied non-uniformly according to the shape or orientation of the blade relative to scaffold surface at the final crimp diameter. The coating may be applied over both the edge and the surface proximal the edge that contacts the scaffold when the iris is at a larger diameter. Or the coating may be limited to the edge to only compensate for damage believed to occur primarily when the iris approaches the final crimped diameter. The thickness and/or distribution of coating over the blade may be selected based on a need to maintain a minimum rate of heat convection across the contacting surface or radiated heat from the exposed metal surface to the scaffold surface, or based on the particular blade design and/or where in the crimping sequence damage is believe to most likely occur, e.g., at the final crimp or earlier in the crimping sequence.

In other embodiments the blade edge may be configured to receive a removable polymer insert, or edge to facilitate more efficient upkeep and reduce downtimes over embodiments that use a polymer coating. An example of such an insert is described in U.S. Pat. No. 7,389,670. Inserts, as opposed to an applied coating, however, can only be made so small and/or thin to enable the insert to be easily secured to, and removed from the blade edge. As such, a blade that uses a polymer insert, e.g., as disclosed in U.S. Pat. No. 7,389,670 may introduce thermal insulation problems between the blades and the scaffold. As such, it may not be desirable to use an insert when the metal surfaces of the blades are needed to conduct heat to the polymer scaffold.

Figure 7A:
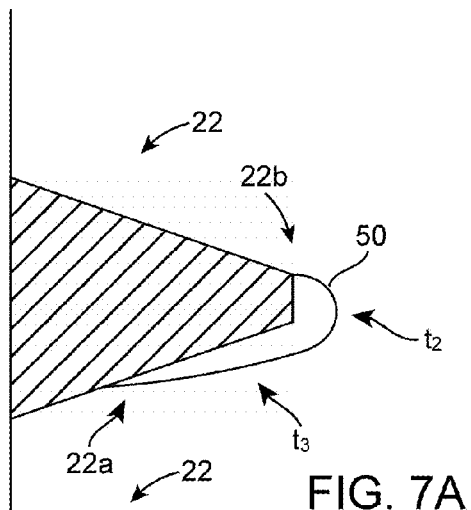
FIGS. 7A and 7B show a first and second disclosure of a polymer coating for a crimper blade. The coatings have the effect of making the blade edge softer so as to reduce damaging indentations and cutting or gouging into the scaffold when the scaffold is brought into contact with a relatively hard and sharp crimper blade edge.
Figure 7B:
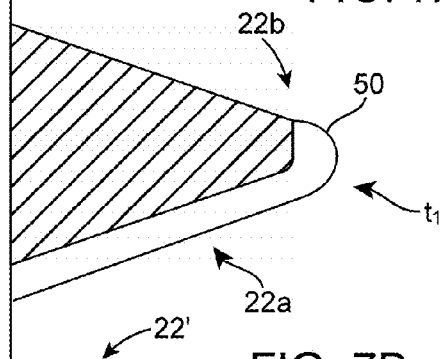

Embodiments are illustrated in FIGS. 7A and 7B. In FIG. 7A, the coating 50 on blade 22 has a first thickness t2 at the leading edge 22b which tapers to a third, reduce thickness t3 away from the leading edge at surface 22a. In FIG. 7B, a generally constant thickness "t1" of coating 50 is applied at the edge 22b and over the surface 22a, which contacts the strut surface before the leading edge 22b during the crimping process.

Figure 7C:
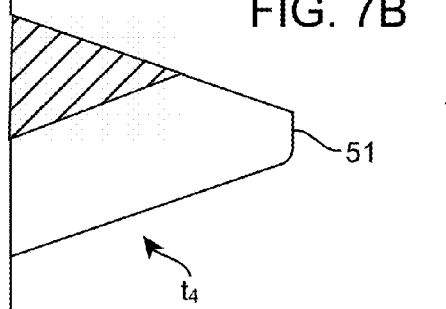
FIG. 7C shows a replaceable polymer insert for a blade for reducing damage to a polymer scaffold.

FIG. 7C depicts a blade 22' formed to receive a polymer insert 51. The insert has about the same thickness t4 over the distance the scaffold makes contact with the blade surface and is shaped to approximately form the edge and surface dimensions of the blades of FIGS. 7A-7B. As can be appreciated by comparing the relative thicknesses, when a replaceable insert is used (FIG. 7C) the insert can thermally insulate the metal blade from the scaffold, which is not desired when blade heat is used to heat the scaffold as in the preferred embodiments. Thus, for embodiments of invention in which a polymer scaffold is heated by the blades, a coating is used which can have a thickness that does not adversely impact heat convection or radiation from the blades to the scaffold.

In other embodiments the blade edge 22b may be reshaped to provide a more blunted or rounded edge to reduce force concentrations on the scaffold surface when the iris approaches the final crimped diameter. The objective sought for such a blade tip may be two-fold. First, by providing a more rounded or blunted edge or tip (a rounded edge being one embodiment of a blunted edge) the surface-to-surface contact area between the blade and scaffold can be made more constant throughout the crimping steps. This has the effect of reducing damaging force concentrations produced by a narrow blade edge, which force concentrations result from a narrow contact area over which the blade applies the crimping force near the final crimping diameter. As such, by increasing the surface area over which the blade acts on the scaffold indentions can be reduced. Second, by providing a blunted edge free from relatively dramatic changes in the surface over which the blade acts on the scaffold, especially when blades become misaligned (e.g., as a result of crimper bearings beginning to wear), any previously irregularly deformed scaffold struts caused by prior crimping steps in a crimping sequence will have less tendency of being caught, grabbed, or pushed outwardly or inwardly by a blade edge. It is believed that significant damage may occur during the final crimping steps from this type of interaction between a blade edge and a previously deformed strut.

Figure 8A:
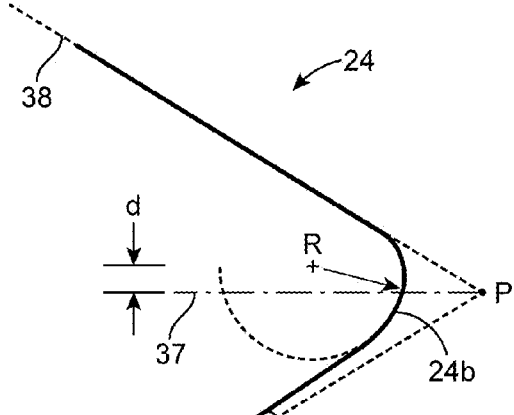
FIGS. 8A-8B shows modified crimper blade edges intended for reducing damage to a polymer scaffold.
Figure 8B:
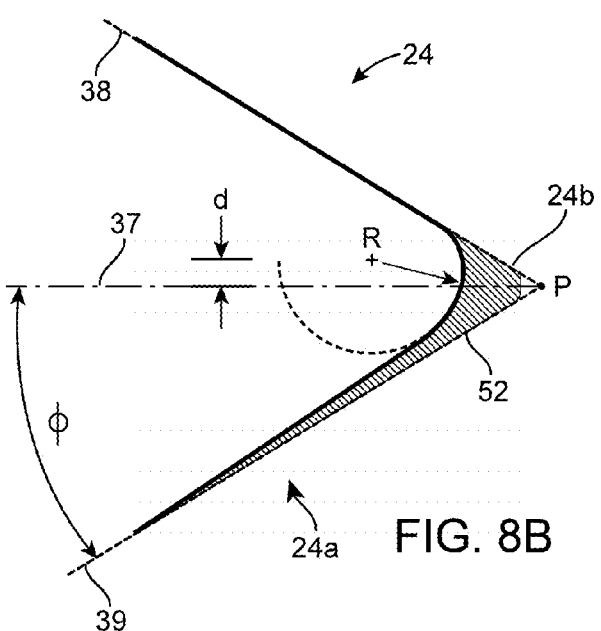

An example of these embodiments is illustrated in FIGS. 8A and 8B (the width of the blade 24 is exaggerated in this view, as compared to FIGS. 7A-7C, for ease of illustration). These drawings show a blade 24 edge that has been modified to make it blunter. In these examples the edge is made rounded. The blade edge 24b has a curvature defined by a radius of curvature R with the center of the circle being offset by a distance "d" from a bisecting line 37 of the converging surfaces 38, 39 that define the width of a wedge that terminates at a reference point "p". For example, if there are twelve crimper blades that cooperate to form the iris, then each blade defines a wedge spanning 30 degrees. Therefore, the angle φ in FIG. 8B is 15 degrees. The bisecting line 37 may correspond to the line of action of the blade 24 when it moves inward by the mechanism of the crimping assembly (FIG. 9). The blade edge may be asymmetric with respect to the bisecting line 37.

As the blade 24 rotates counterclockwise in FIGS. 8A-8B (corresponding to a smaller iris) the blunt edge 24b of the blade 24 more or less maintains the same amount of surface-to-surface contact with the scaffold surface as the preceding surface 24a did when the scaffold had a larger diameter. By maintaining the same surface contact per blade, force concentrations on the scaffold surface resulting in indentations should be reduced. The surface 24a, which contacts the scaffold surface at larger radii of the iris, is sloped to provide a gradual change in curvature leading to the radius of curvature at the edge 24b. Abrupt changes in the surface contour of the blade 24 are not desired so that force concentrations can be avoided when the blade bears down on the scaffold.

FIG. 8B shows a polymer coating 52 applied to the blunted edge, which may be beneficial as a measure to form a more circular iris at the smaller diameters, or to reduce the blade hardness. Despite being blunted, the blade of FIG. 8A may still damage the scaffold when it abuts the relatively soft surface of the scaffold. As can be appreciated by comparing the outer surface of the coated and blunted edge embodiment of FIG. 8B with the other drawings of the blade edge, the blade 24 has about the same surface contours as blade 22 without the coating applied. In cases where the polymer coating is formed to mimic the sharp edge of the convention blade tip, the polymer used for coating 52 may be less elastic or harder since it is formed into a narrow edge. In this way, the polymer edge will have more ability to retain its shape after several scaffold are crimped using a blade configured in this manner.

There are also beneficial effects of forming a blunted, asymmetric edge like that shown in FIGS. 8A-8B relating to avoiding twisting, bending or overlapping struts. When a relatively pointed blade edge, e.g., as depicted in U.S. Pat. No. 7,389,670, bears down on a strut, it can contact or catch a side surface of a strut to cause the strut to bend outwardly or inwardly, especially when the strut was previously bent outwardly or inwardly when the scaffold was being crimped at a larger diameter. By forming a more blunt edge, the edge will have more of a tendency to slide over the edge as the iris diameter is decreased, rather than catching or grabbing the previously bent or twisted strut at its side surface.

It should be pointed out that crimping assemblies heretofore proposed for metal stents have suggested the opposite approach to that illustrated in FIGS. 7-8. Others have proposed making the blade tips more inwardly curved so that when the blades come together at the final diameter the iris will form a more circular shape. However, it is believed this approach would actually exacerbate the problems the inventors are attempting to solve for polymer scaffolds, because, in general, it is difficult to maintain perfect alignment of the blades. An inwardly curved tip for the blade can actually increase damage to a polymer scaffold since an exposed leading edge is then brought more directly into the surface of the scaffold when the iris approaches the final crimped diameter, unless the blades are always maintained in perfect alignment. In this example it is seen that the art pertaining to metal stent crimper devices has proceeded in a direction opposite to that proposed by the inventors. Indeed, based on the known art, it appears there has heretofore been little concern over whether a crimper blade might form indentations, cutting, tearing, or twisting of softer material used to form medical devices, such as a polymer scaffold, which the inventors have found are highly susceptible to damage resulting in loss of strength or improper deployment.

As noted above, according to the disclosure a scaffold has the scaffold pattern described in U.S. application Ser. No. 12/447,758 (US 2010/0004735). Other examples of scaffold patterns suitable for PLLA are found in US 2008/0275537.

FIG. 5 shows a detailed view of an intermediate portion 216 of a strut pattern 200 depicted in US 2010/0004735. The intermediate portion includes rings 212 with linear ring struts 230 and curved hinge elements 232. The ring struts 230 are connected to each other by hinge elements 232. The hinge elements 232 are adapted to flex, which allows the rings 212 to move from a non-deformed configuration to a deformed configuration. Line B-B lies on a reference plane perpendicular to the central axis 224 depicted in US 2010/0004735. When the rings 212 are in the non-deformed configuration, each ring strut 230 is oriented at a non-zero angle X relative to the reference plane. The non-zero angle X is between 20 degrees and 30 degrees, and more narrowly at or about 25 degrees. Also, the ring struts 230 are oriented at an interior angle Y relative to each other prior to crimping. The interior angle Y is between 120 degrees and 130 degrees, and more narrowly at or about 125 degrees. In combination with other factors such as radial expansion, having the interior angle be at least 120 degrees results in high hoop strength when the scaffold is deployed. Having the interior angle be less than 180 degrees allows the scaffold to be crimped while minimizing damage to the scaffold struts during crimping, and may also allow for expansion of the scaffold to a deployed diameter that is greater than its initial diameter prior to crimping. Link struts 234 connect the rings 212. The link struts 234 are oriented parallel or substantially parallel to a bore axis of the scaffold. The ring struts 230, hinge elements 232, and link struts 234 define a plurality of W-shape closed cells 236. The boundary or perimeter of one W-shape closed cell 236 is darkened in FIG. 5 for clarity. In FIG. 5, the W-shapes appear rotated 90 degrees counterclockwise. Each of the W-shape closed cells 236 is immediately surrounded by six other W-shape closed cells 236, meaning that the perimeter of each W-shape closed cell 236 merges with a portion of the perimeter of six other W-shape closed cells 236. Each W-shape closed cell 236 abuts or touches six other W-shape closed cells 236.

Referring to FIG. 5, the perimeter of each W-shape closed cell 236 includes eight of the ring struts 230, two of the link struts 234, and ten of the hinge elements 232. Four of the eight ring struts form a proximal side of the cell perimeter and the other four ring struts form a distal side of the cell perimeter. The opposing ring struts on the proximal and distal sides are parallel or substantially parallel to each other. Within each of the hinge elements 232 there is an intersection point 238 toward which the ring struts 230 and link struts 234 converge. There is an intersection point 238 adjacent each end of the ring struts 230 and link struts 234. Distances 240 between the intersection points adjacent the ends of rings struts 230 are the same or substantially the same for each ring strut 230 in the intermediate portion 216 of the strut pattern 200. The distances 242 are the same or substantially the same for each link strut 234 in the intermediate portion 216. The ring struts 230 have widths 237 that are uniform in dimension along the individual lengthwise axis 213 of the ring strut. The ring strut widths 234 are between 0.15 mm and 0.18 mm, and more narrowly at or about 0.165 mm. The link struts 234 have widths 239 that are also uniform in dimension along the individual lengthwise axis 213 of the link strut. The link strut widths 239 are between 0.11 mm and 0.14 mm, and more narrowly at or about 0.127 mm. The ring struts 230 and link struts 234 have the same or substantially the same thickness in the radial direction, which is between 0.10 mm and 0.18 mm, and more narrowly at or about 0.152 mm.

As shown in FIG. 5, the interior space of each W-shape closed cell 236 has an axial dimension 244 parallel to line A-A and a circumferential dimension 246 parallel to line B-B. The axial dimension 244 is constant or substantially constant with respect to circumferential position within each W-shape closed cell 236 of the intermediate portion 216. That is, axial dimensions 244A adjacent the top and bottom ends of the cells 236 are the same or substantially the same as axial dimensions 244B further away from the ends. The axial and circumferential dimensions 244, 246 are the same among the W-shape closed cells 236 in the intermediate portion 216.

It will be appreciated from FIG. 5 that the strut pattern for a scaffold that comprises linear ring struts 230 and linear link struts 234 formed from a radially expanded and axially extended polymer tube. The ring struts 230 define a plurality of rings 212 capable of moving from a non-deformed configuration to a deformed configuration. Each ring has a center point, and at least two of the center points define the scaffold central axis. The link struts 234 are oriented parallel or substantially parallel to the scaffold central axis. The link struts 234 connect the rings 212 together. The link struts 232 and the ring struts 230 defining W-shape closed cells 236. Each W-shaped cell 236 abuts other W-shaped cells. The ring struts 230 and hinge elements 232 on each ring 212 define a series of crests and troughs that alternate with each other. Each crest on each ring 212 is connected by one of the link struts 234 to another crest on an immediately adjacent ring, thereby forming an offset "brick" arrangement of the W-shaped cells.

Referring to the scaffold pattern 300 depicted in FIG. 6, there are cylindrical rings 305 formed as connected diamond-like cells 310, each ring 305 being interconnected by horizontal linking elements 355. The bending elements 320, 315, 335, 340, 345 form the cells 310. The cells are connected at ends 360.

According to other embodiments a scaffold has a scaffold pattern as depicted in FIG. 10. Examples of this scaffold pattern as described in U.S. patent application Ser. No.

12/561,971. The scaffold pattern 400 includes a plurality of zig-zag like annular bands 306, 308. Each annular band is connected by a horizontal linking element 304.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for crimping a polymer scaffold to a balloon, comprising:
    providing a crimping assembly for crimping the scaffold from a first diameter to a second diameter, the crimping assembly including a plurality of movable blades, each blade having a hardness, a first side and a second side converging to form a tip, the tips being arranged to collectively form an iris about a rotational axis, the iris defining a crimp aperture about which the movable blades are disposed;
    disposing a polymer material between edges of the blade tips and a scaffold surface to reduce the hardness in the blade edges;
    supporting the scaffold while the scaffold is disposed within the iris including inflating a balloon within the scaffold to provide interior support to the scaffold, whereby adjacent struts of the scaffold twisted irregularly by a crimper blade are supported by a balloon surface to deter one of the struts from overlapping or twisting irregularly relative to another of the struts; and
    displacing the plurality of movable blades from a first crimp head diameter to a second crimp head diameter to reduce the diameter of the scaffold from the first diameter to the second diameter, respectively.

2. The method of claim 1, wherein the polymer material is a coating disposed on a leading edge of the blade.

3. The method of claim 2, wherein the coating has a uniform thickness.

4. The method of claim 2, wherein the coating has a coating thickness that tapers away from the leading edge of a blade and along a side that contacts the scaffold surface when the scaffold has the first diameter.

5. The method of claim 1, wherein the scaffold has ring structures forming a tubular body having a distal end, a proximal end, and an intermediate segment between the distal and proximal ends, the ring structures connected to each other by link struts oriented axially, the ring structures and link struts forming W-shape cells, and
    wherein the inflating step includes maintaining a position of a first ring structure relative to an adjacent, second ring structure by the balloon being inflated during the diameter reduction and/or after the diameter reduction.

6. The method of claim 1, wherein the scaffold has zigzag annular bands connected by linking elements, and wherein the first diameter of the scaffold is about 2.5 to 3 times larger than the second diameter of the scaffold.

7. The method of claim 1, wherein the scaffold has zigzag annular bands connected by linking elements, and wherein the balloon has a constant pressure during the diameter reduction.

8. The method of claim 1, wherein a balloon pressure is decreased during the diameter reduction.

9. The method of claim 1, wherein the scaffold has annular bands connected by linking elements, and wherein the balloon is a disposable support balloon used to support the scaffold when the scaffold has the first diameter, wherein the scaffold is reduced in diameter by about 30-40% when reduced from the first diameter to the second diameter, and
    further including the step of reducing the scaffold from the second diameter to a third diameter, including placing the scaffold on the scaffold delivery balloon before reducing the diameter to the third diameter.

10. The method of claim 1, wherein the scaffold has an elevated temperature during the diameter reduction, the scaffold is made from a polymer having a glass transition temperature, and wherein the elevated temperature is the polymer glass transition temperature or 5-10 degrees below the glass transition temperature.

11. The method of claim 10, wherein the polymer includes poly(L-lactide) and the elevated temperature is between about 45 and 54 degrees Celsius.

12. A method for crimping a polymer scaffold to a balloon, comprising:
    providing a crimping assembly for crimping the scaffold from a first diameter to a second diameter, the crimping assembly including a plurality of movable blades, each blade having a hardness, a first side and a second side converging to form a tip, the tips being arranged to collectively form an iris about a rotational axis, the iris defining a crimp aperture about which the movable blades are disposed;
    disposing a polymer material between edges of the blade tips and a scaffold surface;
    supporting the scaffold while the scaffold is disposed within the iris;
    heating the scaffold to a glass transition temperature (Tg) of the polymer of the scaffold, or 5 to 10 degrees below Tg;
    displacing the plurality of movable blades from a first crimp head diameter to a second crimp head diameter to reduce the diameter of the heated scaffold from the first diameter to the second diameter, respectively; and
    after the scaffold has been crimped to the balloon, placing the crimped scaffold and balloon in a restraining sheath.

13. The method of claim 12, wherein the scaffold has a pattern of rings, wherein adjacent rings are connected by links, and the rings and links form a plurality of cells,
    wherein a cell is formed by a first ring portion, a second ring portion and two links connecting the ring portions to each other, and both the first and second ring portions have 1 crown connected to a link that connects to an adjacent ring adjacent the respective first and second ring portion, and 4 crowns not connected to a link.

14. The method of claim 12, wherein following the diameter reduction the scaffold is placed on a catheter comprising the balloon.

15. A method for crimping a polymer scaffold to a balloon, comprising:
    providing a crimping assembly for crimping the scaffold from a first diameter to a second diameter, the crimping assembly including a plurality of movable blades, each blade having a hardness, a first side and a second side converging to form a tip, the tips being arranged to collectively form an iris about a rotational axis, the iris defining a crimp aperture about which the movable blades are disposed;
    disposing a polymer material between edges of the blade tips and a scaffold surface;
    supporting the scaffold while the scaffold is disposed within the iris; and
    displacing the plurality of movable blades from a first crimp head diameter to a second crimp head diameter to reduce the diameter of the scaffold from the first diameter to the second diameter, respectively;

wherein the scaffold has a pattern of rings, wherein adjacent rings are connected by links, and the rings and links form a plurality of cells, wherein a cell is formed by a first ring portion, a second ring portion and two links connecting the ring portions to each other, and both the first and second ring portions have 1 crown connected to a link that connects to an adjacent ring adjacent the respective first and second ring portion, and 4 crowns not connected to a link; and after the scaffold has been crimped to the balloon, placing the crimped scaffold and balloon in a restraining sheath.

16. The method of claim 15, wherein the balloon is inflated after the diameter reduction and before the scaffold and balloon are placed in the restraining sheath.

17. The method of claim 16, wherein the balloon is inflated to retain the scaffold on the balloon.

18. The method of claim 15, wherein after the diameter reduction the scaffold is placed on a catheter comprising the balloon.

19. The method of claim 18, wherein the scaffold is placed on a support balloon before the diameter reduction.

20. The method of claim 15, wherein the scaffold has an elevated temperature during diameter reduction, the scaffold is made from a polymer having a glass transition temperature, and wherein the elevated temperature is the polymer glass transition temperature or 5-10 degrees below the glass transition temperature.

* * * * *